US011786510B2

(12) United States Patent
Lin et al.

(10) Patent No.: US 11,786,510 B2
(45) Date of Patent: Oct. 17, 2023

(54) PHARMACEUTICAL COMPOSITIONS AND INTRAVITREAL DRUG DELIVERY SYSTEMS FOR THE TREATMENT OF OCULAR DISEASES

(71) Applicant: Perfuse Therapeutics, Inc., San Francisco, CA (US)

(72) Inventors: Cheng-Wen Lin, Cary, NC (US); Angela Dawn Glendenning, Raleigh, NC (US); Sevgi Gurkan, Belmont, CA (US)

(73) Assignee: Perfuse Therapeutics, Inc., San Francisco, CA (US)

( * ) Notice: Subject to any disclaimer, the term of this patent is extended or adjusted under 35 U.S.C. 154(b) by 0 days.

(21) Appl. No.: 18/060,503

(22) Filed: Nov. 30, 2022

(65) Prior Publication Data

US 2023/0105507 A1  Apr. 6, 2023

Related U.S. Application Data

(63) Continuation of application No. PCT/US2022/027048, filed on Apr. 29, 2022.

(60) Provisional application No. 63/287,737, filed on Dec. 9, 2021, provisional application No. 63/182,559, filed on Apr. 30, 2021.

(51) Int. Cl.
*A61K 31/422* (2006.01)
*A61K 9/00* (2006.01)
*A61K 47/34* (2017.01)

(52) U.S. Cl.
CPC .......... *A61K 31/422* (2013.01); *A61K 9/0051* (2013.01); *A61K 47/34* (2013.01)

(58) Field of Classification Search
CPC ...... A61K 31/422; A61K 47/34; A61K 45/09; A61K 9/0024; A61P 27/02
See application file for complete search history.

(56) References Cited

U.S. PATENT DOCUMENTS

| | | | |
|---|---|---|---|
| 5,364,374 A | 11/1994 | Morrison et al. | |
| 6,043,265 A * | 3/2000 | Murugesan | A61P 9/04 548/236 |
| 7,927,613 B2 * | 4/2011 | Almarsson | A61K 47/10 514/217 |
| 8,980,874 B2 | 3/2015 | Gulati | |
| 9,610,246 B2 | 4/2017 | Shiah et al. | |
| 2003/0176356 A1 | 9/2003 | Yorio et al. | |

(Continued)

FOREIGN PATENT DOCUMENTS

WO   WO-2002/032884 A2   4/2002
WO   WO-2010/144477 A2   12/2010

(Continued)

OTHER PUBLICATIONS

U.S. Appl. No. 17/733,310, filed Apr. 29, 2022.

(Continued)

*Primary Examiner* — Carlos A Azpuru
(74) *Attorney, Agent, or Firm* — Goodwin Procter LLP

(57) ABSTRACT

The present disclosure relates to a biodegradable ocular implant comprising a biodegradable polymer containing a compound such as Edonentan, or a pharmaceutically acceptable salt thereof. Also disclosed are methods of treatment of ocular diseases with the biodegradable ocular implant and methods of preparation of the same.

4 Claims, 16 Drawing Sheets

(56) References Cited

U.S. PATENT DOCUMENTS

| | | | |
|---|---|---|---|
| 2004/0063731 | A1 | 4/2004 | Eggenweiler et al. |
| 2004/0234611 | A1 | 11/2004 | Ahlheim et al. |
| 2007/0116729 | A1 | 5/2007 | Palepu |
| 2007/0260203 | A1 | 11/2007 | Donello et al. |
| 2009/0054473 | A1 | 2/2009 | Roden et al. |
| 2011/0275715 | A1 | 11/2011 | Mashima et al. |
| 2015/0118279 | A1 | 4/2015 | Ghebremeskel et al. |
| 2016/0331712 | A1 | 11/2016 | Georgiou |
| 2016/0346224 | A1* | 12/2016 | Macdonald ........ A61K 31/4422 |
| 2018/0110728 | A1 | 4/2018 | Duran Muiños et al. |
| 2018/0362570 | A1 | 12/2018 | Ganapati et al. |
| 2019/0015521 | A1* | 1/2019 | Roizman ................ A61P 29/00 |
| 2020/0230157 | A1 | 7/2020 | Williams et al. |
| 2020/0306182 | A1 | 10/2020 | Das et al. |
| 2022/0257505 | A1 | 8/2022 | Gurkan et al. |
| 2022/0257568 | A1 | 8/2022 | Gurkan et al. |

FOREIGN PATENT DOCUMENTS

| | | | |
|---|---|---|---|
| WO | WO-2016/156639 | A1 | 10/2016 |
| WO | WO-2017/217967 | A1 | 12/2017 |
| WO | WO-2018/185516 | A1 | 10/2018 |
| WO | WO-2019/210194 | A1 | 10/2019 |
| WO | WO-2021/087399 | A1 | 5/2021 |
| WO | WO-2021/158663 | A1 | 8/2021 |

OTHER PUBLICATIONS

U.S. Appl. No. 17/733,216, filed Apr. 29, 2022.

U.S. Appl. No. 17/879,627, filed Aug. 2, 2022.

Davenport, et al., "Endothelin." Pharmacological reviews (2016) 68:357-418.

Francesco Boscia, Current Approaches to the Management of Diabetic Retinopathy and Diabetic Macular Oedema, 70 DRUGS 2171 (Year: 2010).

Hulpke-Wette, et al., "BMS-193884 and BMS-207940 Bristol-Myers Squibb" Current Opinion in Investigational Drugs (2002), 3(7), 1057-1061.

International Search Report and Written Opinion dated Feb. 3, 2021, for International Application No. PCT/US2020/058411 filed Oct. 30, 2020. (8 pages).

International Search Report and Written Opinion dated Sep. 14, 2022, for International Application No. PCT/US2022/27048 filed Apr. 29, 2022. (12 pages).

International Search Report of International Application No. PCT/US2021/016414 dated Apr. 15, 2021, 4 pages.

PUBCHEM-SID:376333874 Deposit Date: Nov. 30, 2018 (Nov. 30, 2018) pp. 1-6; p. 2.

Rosenthal Rita et al., "Endothelin Antagonism as an Active Principle for Glaucoma Therapy." British Journal of Pharmacology (2011) 162, 806-816.

Sasaoka et al., "Intravitreal injection of endothelin-1 caused optic nerve damage following to ocular hypoperfusion in rabbits" Experimental Eye Research 83 (2006) 629-637.

Shoshani, et al., "Endothelin and its suspected role in the pathogenesis and possible treatment of glaucoma" Current Eye Research 37(1), 1-11, 2012.

Anna-Leena Siren, et al., Endothelin B Receptor Deficiency Augments Neuronal Damage Upon Exposure to Hypoxia-Ischemia In Vivo, 945 Brain Res. 144 (Year:2002).

Goto et al. "Molecular Pharmacology and Pathophysiological Significance of Endothelin" Jpn. J. Pharmacol. 72, 261-290 (1996).

J.W. Kiel "Endothelin Modulation of Choroidal Blood Flow in the Rabbit" Exp Eye Res. 2000, 71 (6), pa es 543-550.

Li et al. "Endothelin and Diabetic Complications: a Brain-Centric View" Physiol. Res. 67 (Suppl. 1 ):S83-S94, 2018.

Miglior et al (Current Opinion in Pharmacology, 2013; 13:32-35) (Year: 2013).

Polak et al. Effect of Endothelin and BQ123 on Ocular Blood Flow Parameters in Healthy Sub•ects; Investi ative Ophthalmolo & Visual Science, 2001, 42, 2949-2956.

Prasanna et al. "Effect of elevated intraocular pressure on endothelin-1 in a rat model of laucoma" Pharmacolo ical Research 51 (2005) a es 41-50.

Prasanna et al. "Endothelin, Astrocytes and Glaucoma" Exp Eye Res. Aug. 2011, 93(2), pp. 170-177.

Sidney G. Shaw, et al., "Edonentan Antagonism Prevents Diabetic Retinopahy in NOD Mice: A Potential Role fo the Angiogenic Factor Adrenomedullin," 231 Exp. Bio. Med. 1101 (2006)).

Takagi et al. "Regulation of Retinal Hemodynamics in Diabetic Rats by Increased Expression and Action of Endothelin-1" Investigative Ophthalmology & Visual Science, 1996, 37, 2504-2518.

Vecino et al. "Glaucoma Animal Models" Glaucoma—Basic and Clinical Concepts; www.intecho <http://www.intecho> en.com; pa es 319-335.

Wang and Lo "Diabetic Retinopathy: Pathophysiology and Treatments" Int. J. Mol. Sci., 2018, 19, 1816: do: 10.3390/ijms1906816.

Veurink et al. "Development of an Intravitreal Peptide (BQ123) Sustained Release System Based on Poly(2-Hydroxyoctanoic Acid) Aiming at a Retinal Vasodilator Response" Journal of Ocular Pharmacolo and Thera eutics, 2014, 30, a es 517-523.

Wykoff et al. "Retinal non-perfusion in diabetic retinopathy" Nature, Eye, 2022, 36:249-256.

Sun et al. "Mitophagy protects the retina against anti-vascular endothelial growth factor therapy-driven hypoxia via hypoxia-inducible fact-1 alpha signaling" Front. Cell. Dev. Biol. 9:727822.

Maturi et al. "Four-Year Visual Outcomes in the Protocol W Randomized Trial of Intravitreous Aflibercept for Prevention of Vision-Threatening Complications of Diabetic Retinopathy" JAMA. 2023; 329(5): 376-385.

Allison, K et al. "Epidemiology of Glaucoma: The Past, Present, and Predictions for the Future" Cureus 12(11): Nov. 24, 2020.

Urtii, A. "Challenges and obstacles of ocular pharmacokinetics and drug delivery" Advanced Drug Delivery Reviews 58 (2006) 1131-1135.

Caira et al., "Crystalline Polymorphism of Organic Compounds", Topics in Current Chemistry; Spring Berlin, DE, vol. 198, Jan. 1, 1998, pp. 163-208.

Murugesan et al., "Biphenylsulfonamide Endothelin receptor Antagonists", Journal of Medicinal Chemistry, American Chemical Society, US, vol. 46, No. 1, Nov. 26, 2002, pp. 135-137.

\* cited by examiner

| SCAN: 3.0/44.9933/0.01973/24.78(sec), Cu(40kV,40mA), I(max)=6860, 04/10/20 10:20 |||||||
|---|---|---|---|---|---|---|
| PEAK: 35-pts/Parabolic Filter, Threshold=3.0, Cutoff=0.1%, BG=3/1.0, Peak-Top=Summit |||||||
| NOTE: Intensity = Counts, 2T(0)=0.0(°), Wavelength to Compute d-Spacing = 1.54056A(Cu/K-alpha1) |||||||
| # | 2-Theta | d(A) | Height | I% | Area | I% | FWHM |
| 1 | 5.641 | 15.6528 | 1393 | 20.3 | 13553 | 24.5 | 0.187 |
| 2 | 8.803 | 10.0363 | 563 | 8.2 | 3809 | 6.9 | 0.180 |
| 3 | 9.256 | 9.5470 | 504 | 7.3 | 2976 | 5.4 | 0.169 |
| 4 | 10.494 | 8.4231 | 818 | 11.9 | 4742 | 8.6 | 0.134 |
| 5 | 11.367 | 7.7780 | 6860 | 100.0 | 55374 | 100.0 | 0.140 |
| 6 | 12.198 | 7.2497 | 434 | 6.3 | 1350 | 2.4 | 0.117 |
| 7 | 14.408 | 6.1424 | 951 | 13.9 | 6234 | 11.3 | 0.141 |
| 8 | 15.072 | 5.8734 | 484 | 7.1 | 1747 | 3.2 | 0.110 |
| 9 | 15.710 | 5.6362 | 764 | 11.1 | 4042 | 7.3 | 0.124 |
| 10 | 16.773 | 5.2814 | 839 | 12.2 | 3958 | 7.1 | 0.113 |
| 11 | 17.739 | 4.9959 | 2150 | 31.3 | 20631 | 37.3 | 0.183 |
| 12 | 18.629 | 4.7591 | 595 | 8.7 | 1999 | 3.6 | 0.109 |
| 13 | 19.280 | 4.5989 | 3173 | 46.3 | 23625 | 42.7 | 0.137 |
| 14 | 19.733 | 4.4952 | 608 | 8.9 | 3384 | 6.1 | 0.180 |
| 15 | 20.295 | 4.3721 | 536 | 7.8 | 2106 | 3.8 | 0.151 |
| 16 | 21.132 | 4.2006 | 1439 | 21.0 | 8311 | 15.0 | 0.124 |
| 17 | 21.907 | 4.0538 | 1206 | 17.6 | 11523 | 20.8 | 0.222 |
| 18 | 22.495 | 3.9493 | 795 | 11.6 | 3003 | 5.4 | 0.112 |
| 19 | 23.365 | 3.8041 | 903 | 13.2 | 4778 | 8.6 | 0.141 |
| 20 | 23.938 | 3.7143 | 1304 | 19.0 | 7676 | 13.9 | 0.133 |
| 21 | 24.624 | 3.6123 | 995 | 14.5 | 7730 | 14.0 | 0.189 |
| 22 | 26.073 | 3.4148 | 595 | 8.7 | 2572 | 4.6 | 0.146 |
| 23 | 26.718 | 3.3338 | 722 | 10.5 | 7595 | 13.7 | 0.294 |
| 24 | 28.674 | 3.1107 | 412 | 6.0 | 1069 | 1.9 | 0.142 |
| 25 | 29.141 | 3.0619 | 398 | 5.8 | 754 | 1.4 | 0.098 |
| 26 | 30.115 | 2.9650 | 440 | 6.4 | 3479 | 6.3 | 0.309 |
| 27 | 30.841 | 2.8969 | 437 | 6.4 | 1605 | 2.9 | 0.152 |
| 28 | 33.588 | 2.6660 | 345 | 5.0 | 2082 | 3.8 | 0.259 |

PHARMACEUTICAL COMPOSITIONS AND INTRAVITREAL DRUG DELIVERY SYSTEMS FOR THE TREATMENT OF OCULAR DISEASES

RELATED APPLICATIONS

This application is a continuation of International Application Number PCT/US2022/027048, filed on Apr. 29, 2022, which claims priority to U.S. Provisional Patent Application Nos 63/182,559, filed on Apr. 30, 2021, and 63/287,737, filed on Dec. 9, 2021, the entire contents of each of which are hereby incorporated by reference for all purposes.

BACKGROUND

Examples of debilitating ocular diseases include glaucoma, diabetic retinopathy (DR), retinal vein occlusion (RVO), and retinopathy of prematurity (ROP). These ocular diseases can variously cause long-term damage to the eye and, ultimately, blindness. While neonates, the young, adults of all ages and the elderly are affected, only a handful of treatments exist. These treatments are only for a subset of ocular diseases and slow, but do not prevent, blindness. The annual economic burden on the U.S. alone is over $100 billion.

Options for treating the ocular diseases are still very limited largely due to lack of therapeutic efficacy. Efforts have been devoted to enhancing drug therapeutic effectiveness while minimizing side effects in the treatment or amelioration of ocular diseases. One such effort involves development of novel biodegradable ocular implants providing better permeability, treatability, and controlled release at target site.

Edonentan is a highly selective and very potent endothelin A receptor antagonist. Edonentan was developed as a second-generation analog following the discontinuation of the first clinical candidate, BMS-193884, which was being developed for the treatment of congestive heart failure (CHF). Edonentan was in phase I trials by April 2002, but its development was discontinued.

There remains a need to more effectively reduce the incidence of, treat or otherwise ameliorate glaucoma, DR, RVO, and ROP.

BRIEF DESCRIPTION OF THE DRAWINGS

FIG. 17 depicts XRPD characteristic peaks for crystalline Form 4 shown in FIG. 12.

SUMMARY

Figure 1:
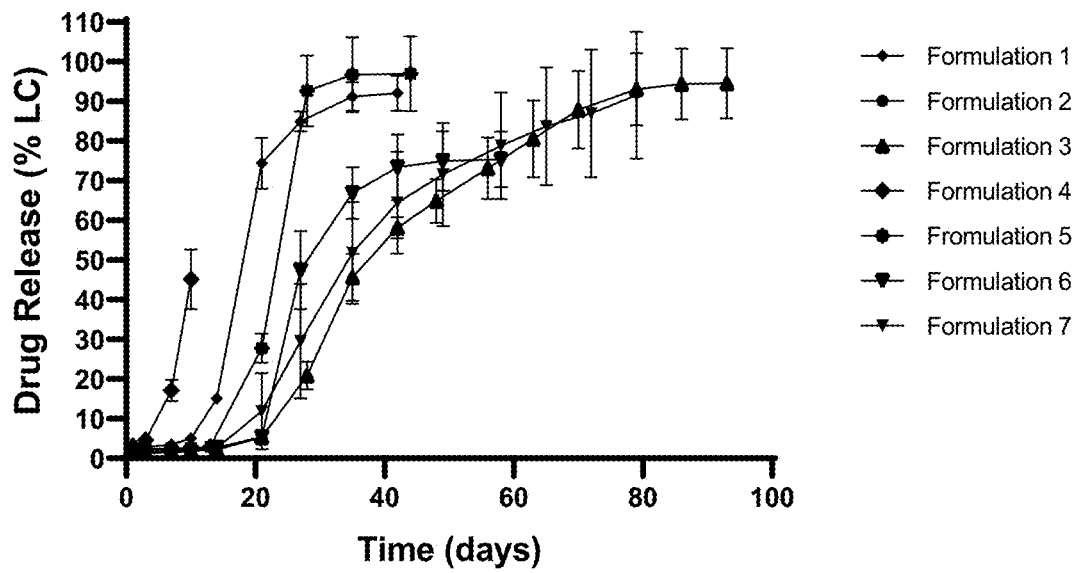
FIG. 1 depicts drug release profiles of Edonentan in disk punches of exemplary formulations each containing a polymer matrix incorporating Edonentan. Up to 70% of Edonentan was released from most formulations within 100 days as determined by high-performance liquid chromatography (HPLC). The in vitro release results show that the amount of Edonentan released decreases with the increase of the ratio of poly-lactic acid (PLA) to poly-glycolic acid (PGA) as well as the increase of molecular weight of the polymer. Formulation 1 (50/50 RG503/RG503H) has a faster release compared to Formulation 2 (65/35 PLA/PGA) due to the lower ratio of PLG to PGA. Formulation 4 (50/50 502/502H) has a faster release compared to Formulation 1 (50/50 503/503H) due to the lower molecular weight of the polymer. The results also showed that RG753S has the slowest release profile among the formulations tested, and the mixtures of RG753S with other faster-releasing formulations provide a long period of sustained drug release while maintaining sufficient drug release at earlier time points.

The present disclosure provides a biodegradable ocular implant and use of the same for treating an ocular disease selected from glaucoma, diabetic retinopathy (DR), retinal vein occlusion (RVO), and retinopathy of prematurity (ROP). In some embodiments, the biodegradable ocular implant comprises a biodegradable polymer containing a compound selected from the group consisting of Edonentan, Tezosentan, A-182086, Clazosentan, S1255, ACT-132577, Enrasentan, and Sparsentan, or a pharmaceutically acceptable salt thereof. Preferably, in embodiments, the biodegradable ocular implant comprises a biodegradable polymer containing a compound of Formula I:

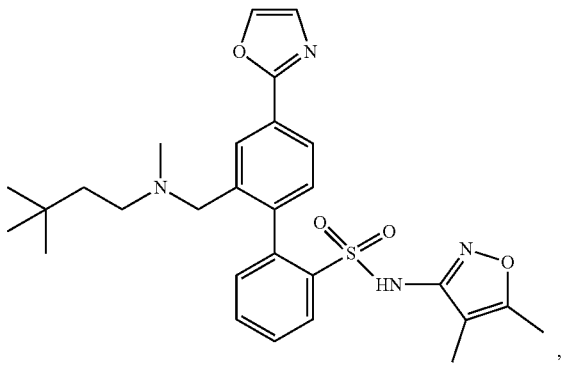

(I)

or a pharmaceutically acceptable salt thereof.

The present disclosure also provides a method of treating an ocular disease, comprising contacting an optical tissue in a subject with a biodegradable ocular implant described herein, wherein the ocular disease is selected from the group consisting of glaucoma, diabetic retinopathy (DR), retinal vein occlusion (RVO), and retinopathy of prematurity (ROP), and the compound is present in an amount therapeutically effective for treating the ocular disease.

Also provided herein is a method of manufacturing an ocular delivery device. The method comprises subjecting a biodegradable polymer containing a compound incorporated therein to an injection molding, wherein the compound is a compound of Formula I:

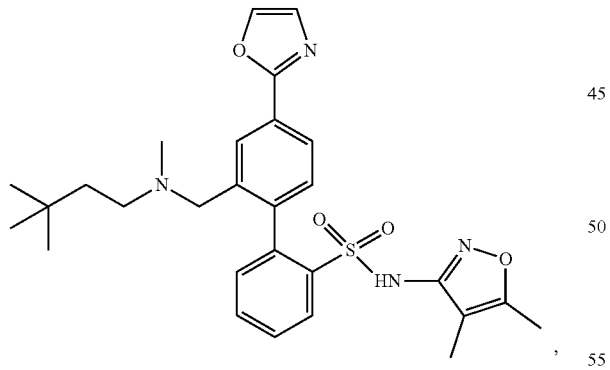

(I)

or a pharmaceutically acceptable salt thereof.

The details of one or more embodiments of the disclosure are set forth in the description below. Other features, objects, and advantages of the disclosure will be apparent from the below drawings, description and from the claims.

DETAILED DESCRIPTION

The present disclosure arises from the discovery that certain biodegradable ocular implants comprising a biodegradable polymer containing a compound incorporated therein, wherein the compound is, preferably, Edonentan, are suitable for the prevention, treatment, or otherwise amelioration of ocular diseases including, but not limited to, glaucoma, diabetic retinopathy (DR), retinal vein occlusion (RVO), and retinopathy of prematurity (ROP). The disclosure is further described below.

Compounds

The biodegradable ocular implants described herein and methods of use thereof comprise a biodegradable polymer containing a compound described herein, for example, Edonentan, Tezosentan, A-182086, Clazosentan, S1255, ACT-132577, Enrasentan, and Sparsentan, or a pharmaceutically acceptable salt thereof. It can be appreciated that the contemplated compounds herein are endothelin receptor antagonists.

In certain embodiments, the compound is a compound of Formula I:

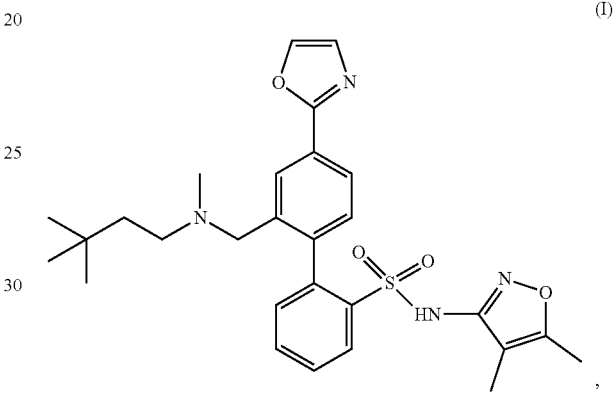

(I)

or a pharmaceutically acceptable salt thereof. The compound of Formula I is also known as Edonentan. Edonentan has the chemical name of N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide (molecular weight of 536.6 g/mol). Methods of preparing Edonentan are well known to a person of skill in the art. Suitable methods are disclosed, for example, in U.S. Pat. No. 6,043,265.

In some embodiments, the compound is A-182086, which has the structure:

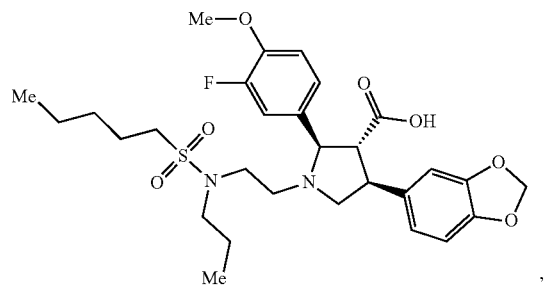 [SMILES: CCCCCS(=O)(=O)N(CCC)CCN1C[C@H](c2ccc3c(c2)OCO3)[C@@H](C(=O)O)[C@@H]1c1ccc(OC)c(F)c1]

or a pharmaceutically acceptable salt thereof.

A-182086 has the chemical name of (2R,3R,4S)-4-(2H-1,3-benzodioxol-5-yl)-2-(3-fluoro-4-methoxyphenyl)-1-[2-(N-propylpentane-1-sulfonamido)ethyl]pyrrolidine-3-carboxylic acid (molecular weight of 578.7 g/mol). Methods of preparing A-182086 are well known to a person of skill in the art. Suitable methods are disclosed, for example, in U.S. Pat. No. 6,162,927.

In various embodiments, the concentration of the compound (e.g., compound of Formula I, A-182086) in the biodegradable ocular implant is present in the biodegradable polymer is about 5% w/w to about 95% w/w (e.g., about 10% w/w to about 95% w/w, about 15% w/w to about 95% w/w, about 20% w/w to about 95% w/w, about 25% w/w to about 95% w/w, about 30% w/w to about 95% w/w, about 35% w/w to about 95% w/w, about 40% w/w to about 95% w/w, about 45% w/w to about 95% w/w, about 50% w/w to about 95% w/w, about 55% w/w to about 95% w/w, about 60% w/w to about 95% w/w, about 65% w/w to about 95% w/w, about 70% w/w to about 95% w/w, about 75% w/w to about 95% w/w, about 80% w/w to about 95% w/w, about 85% w/w, about 95% w/w, about 90% w/w to about 95% w/w, about 5% w/w to about 10% w/w, about 5% w/w to about 15% w/w, about 5% w/w to about 20% w/w, about 5% w/w to about 25% w/w, about 5% w/w to about 30% w/w, about 5% w/w to about 35% w/w, about 5% w/w to about 40% w/w, about 5% w/w to about 45% w/w, about 5% w/w to about 50% w/w, about 5% w/w to about 55% w/w, about 5% w/w to about 60% w/w, about 5% w/w to about 65% w/w, about 5% w/w to about 70% w/w, about 5% w/w to about 75% w/w, about 5% w/w to about 80% w/w, about 5% w/w to about 85% w/w, and about 5% w/w to about 90% w/w). In certain embodiments, the concentration of the compound in the biodegradable ocular implant is present in the biodegradable polymer is about 20% w/w to about 60% w/w (e.g., about 20% w/w to about 55% w/w, about 20% w/w to about 50% w/w, about 20% w/w to about 45% w/w, about 20% w/w to about 40% w/w, about 20% w/w to about 35% w/w, about 20% w/w to about 30% w/w, about 20% w/w to about 25% w/w, about 25% w/w to about 60% w/w, about 30% w/w to about 60% w/w, about 35% w/w to about 60% w/w, about 40% w/w to about 60% w/w, about 45% w/w to about 60% w/w, about 50% w/w to about 60% w/w, about 55% w/w to about 60% w/w). In certain embodiments, the concentration of the compound in the biodegradable ocular implant is present in the biodegradable polymer is about 25% w/w to about 45% w/w. In certain embodiments, the concentration of the compound in the biodegradable ocular implant is present in the biodegradable polymer is about 40% w/w to about 50% w/w (e.g., about 40% w/w to about 45% w/w, about 45% w/w to about 50% w/w). In various embodiments, the concentration of the compound is about 5% w/w, about 10% w/w, about 15% w/w, about 20% w/w, about 25% w/w, about 30% w/w, about 35% w/w, about 40% w/w, about 45% w/w, or about 50% w/w. In various embodiments, the concentration of the compound is about 30% w/w. In various embodiments, the concentration of the compound is about 40% w/w. In various embodiments, the concentration of the compound is about 45% w/w. In various embodiments, the concentration of the compound is about 50% w/w.

In embodiments, the amount of the compound (e.g., compound of Formula I, A-182086) in the biodegradable ocular implant is present in the biodegradable polymer is about 1 µg to about 500 µg (e.g., about 10 µg to about 500 µg, about 20 µg to about 500 µg, about 30 µg to about 500 µg, about 40 µg to about 500 µg, about 50 µg to about 500 µg, about 60 µg to about 500 µg, about 70 µg to about 500 µg, about 80 µg to about 500 µg, about 90 µg to about 500 µg, about 100 µg to about 500 µg, about 100 µg to about 500 µg, about 125 µg to about 500 µg, about 150 µg to about 500 µg, about 175 µg to about 500 µg, about 200 µg to about 500 µg, about 225 µg to about 500 µg, about 250 µg to about 500 µg, about 275 µg to about 500 µg, about 300 µg to about 500 µg, about 325 µg to about 500 µg, about 350 µg to about 500 µg, about 375 µg to about 500 µg, about 400 µg to about 500 µg, about 425 µg to about 500 µg, about 450 µg to about 500 µg, and about 475 µg to about 500 µg). In various embodiments, the amount of the compound (e.g., compound of Formula I, A-182086) in the biodegradable ocular implant is present in the biodegradable polymer is about 70 µg to about 230 µg (e.g., about 70 µg, about 75 µg, about 80 µg, about 85 µg, about 90 µg, about 95 µg, about 100 µg, about 105 µg, about 110 µg, about 115 µg, about 120 µg, about 125 µg, about 130 µg, about 135 µg, about 140 µg, about 145 µg, about 150 µg, about 155 µg, about 160 µg, about 165 µg, about 170 µg, about 175 µg, about 180 µg, about 185 µg, about 190 µg, about 195 µg, about 200 µg, about 205 µg, about 210 µg, about 215 µg, about 220 µg, about 225 µg, and about 230 µg). In various embodiments, the amount of the compound (e.g., compound of Formula I, A-182086) in the biodegradable ocular implant is present in the biodegradable polymer is about 165 µg to about 220 µg (e.g., about 165 µg, about 170 µg, about 175 µg, about 180 µg, about 185 µg, about 190 µg, about 195 µg, about 200 µg, about 205 µg, about 210 µg, about 215 µg, and about 220 µg). In some embodiments, the amount of the compound (e.g., compound of Formula I, A-182086) in the biodegradable ocular implant is present in the biodegradable polymer is about 150 µg to about 250 µg, about 300 µg to about 550 µg, or about 300 µg to about 600 µg. In various embodiments, the amount of the compound (e.g., compound of Formula I, A-182086) in the biodegradable ocular implant is present in the biodegradable polymer is about 330 µg to about 500 µg (e.g., about 330 µg, about 335 µg, about 340 µg, about 345 µg, about 350 µg, about 355 µg, about 360 µg, about 365 µg, about 370 µg, about 375 µg, about 380 µg, about 385 µg, about 390 µg, about 395 µg, about 400 µg, about 405 µg, about 410 µg, about 415 µg, about 420 µg, about 425 µg, about 430 µg, about 435 µg, about 440 µg, about 445 µg, about 450 µg, about 455 µg, about 460 µg, about 465 µg, about 470 µg, about 475 µg, about 480 µg, about 485 µg, about 490 µg, about 495 µg, and about 500 µg).

Biodegradable Polymers

Suitable polymeric materials or compositions for use in the implants described herein include those materials which are compatible, that is biocompatible, with the eye so as to cause no substantial interference with the functioning or physiology of the eye. Such polymeric materials may be biodegradable, bioerodible or both biodegradable and bioerodible.

The term "biodegrade" or "biodegradable" as used herein generally refers to a biologically assisted degradation process that the polymer making-up the implant undergoes in a biological environment, such as within the body of a subject. It would be appreciated that biodegradation encompasses within its scope the processes of absorption, dissolution, breaking down, degradation, assimilation, or otherwise removal of the implant from the body, a biological environment.

The term "polymer" as used herein encompasses both homopolymers (polymers having only one type of repeating unit) and copolymers (a polymer having more than one type of repeating unit).

The term "biodegradable polymer" as used herein refers to a polymer or polymers, which degrade in vivo, under physiological conditions. The release of the therapeutic agent occurs concurrent with, or subsequent to, the degradation of a biodegradable polymer over time.

In preferable embodiments, the biodegradable polymer is a PLGA (poly(lactic-co-glycolic acid)). PLGA polymers are known to degrade via backbone hydrolysis (bulk erosion)

and the final degradation products are lactic and glycolic acids, which are non-toxic and considered natural metabolic compounds. Lactic and glycolic acids are eliminated safely via the Krebs cycle by conversion to carbon dioxide and water.

PLGA is synthesized through random ring-opening copolymerization of the cyclic dimers of glycolic acid and lactic acid. Successive monomeric units of glycolic or lactic acid are linked together by ester linkages. The ratio of lactide to glycolide can be varied, altering the biodegradation characteristics of the product. By altering the ratio, it is possible to tailor the polymer degradation time. Importantly, drug release characteristics are affected by the rate of biodegradation, molecular weight, and degree of crystallinity in drug delivery systems. By altering and customizing the biodegradable polymer matrix, the drug delivery profile can be changed.

PLGA is cleaved predominantly by non-enzymatic hydrolysis of its ester linkages throughout the polymer matrix, in the presence of water in the surrounding tissues. PLGA polymers are biocompatible, because they undergo hydrolysis in the body to produce the original monomers, lactic acid and/or glycolic acid. Lactic and glycolic acids are nontoxic and eliminated safely via the Krebs cycle by conversion to carbon dioxide and water. The biocompatibility of PLGA polymers have been further examined in both non-ocular and ocular tissues of animals and humans. The findings indicate that the polymers are well tolerated.

Examples of PLGA polymers, which may be utilized in an embodiment of the disclosure, include the RESOMER® Product line from Evonik Industries identified as, but are not limited to, RG502, RG502H, RG503, RG503H, RG504, RG504H, RG505, RG653H, RG750S, RG752H, RG752S, RG753H, RG753S, RG755, RG755S, RG756S, RG757S, and RG858S.

Such PLGA polymers include both acid and ester terminated polymers with inherent viscosities ranging from approximately 0.14 to approximately 1.7 dL/g when measured at 0.1% w/v in CHCl$_3$ at 25° C. with an Ubbelhode size 0c glass capillary viscometer. Example polymers used in various embodiments of the disclosure may include variation in the mole ratio of D,L-lactide to glycolide from approximately 50:50 to approximately 85:15, including, but not limited to, 50:50, 65:35, 75:25, and 85:15.

Other examples of PLGA polymers which may be utilized in an embodiment of the disclosure include those produced by Lakeshore Biomaterials identified as, but are not limited to, DLG 1A, DLG 3 A, or DLG 4A. Such DLG polymers include both acid (A) and ester (E) terminated polymers with inherent viscosities ranging from approximately 0.0.5 to approximately 1.0 dL/g when measured at 0.1% w/v in CHCl$_3$ at 25° C. with an Ubbelhode size 0c glass capillary viscometer. Example polymers used in various embodiments of the disclosure may include variation in the mole ratio of D,L-lactide to glycolide from approximately 1:99 to approximately 99:1, including, but not limited to, 50:50, 65:35, 75:25, and 85:15.

RESOMERS® identified by an "RG" or "DLG" in the product name, such as RG752S, is a poly(D,L-lactide-co-glycolide) or PLGA having the general structure (V):

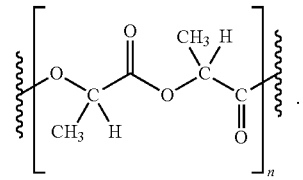

(V)

The synthesis of various molecular weights of DLG with various D,L-lactide-glycolide ratios is possible. In one embodiment, DLG, such as 1A, with an inherent viscosity of approximately 0.05 to approximately 0.15 dL/g can be used. In another embodiment, DLG, such as 2A, with an inherent viscosity of approximately 0.15 to approximately 0.25 dL/g can be used. [0168] Poly(D,L-lactide-co-glycolide) or PLGA copolymers can be synthesized at different ratios of lactide to glycolide, such as a lactide:glycolide ratio of 75:25. These copolymers can be an ester-terminated PLGA copolymer, as identified by the terminal "S" in the product name, or an acid-terminated PLGA copolymer, as identified by the terminal "H" in the product name.

In some embodiments, the biodegradable ocular implant of the disclosure comprises at least one PLGA, wherein each PLGA is independently selected from the group consisting of RG502, RG502S, RG502H, RG503, RG503H, RG504, RG504H, RG505, RG506, RG653H, RG752H, RG752S, RG753H, RG753S, RG755, RG755S, RG756, RG756S, RG757S, RG750S, RG858, and RG858S. In some embodiments, the biodegradable polymer comprises a poly(lactic-co-glycolic acid) (PLGA), wherein the PLGA is selected from the group consisting of RG502, RG503H, RG503, RG752S, RG753S, RG755S, RG756S, and RG858S. In some embodiments, the biodegradable polymer comprises a poly(lactic-co-glycolic acid) (PLGA), wherein the PLGA is selected from the group consisting of RG502, RG503, RG752S, RG753S, RG755S, RG756S, and RG858S. In some embodiments, the biodegradable ocular implant of the disclosure comprises one PLGA. In some embodiments, the PLGA has a ratio of PLA and PLG of about 65:35.

In some embodiments, the biodegradable ocular implant of the disclosure comprises at least two PLGA. In some embodiments, the biodegradable polymer comprises at least three PLGA (e.g., three to six PLGA, three PLGA, four PLGA, five PLGA).

In some embodiments, the biodegradable ocular implant of the disclosure comprises at least two PLGA, wherein each PLGA is independently selected from the group consisting of RG502, RG502H, RG503, RG503H, RG504, RG504H, RG505, RG653H, RG750S, RG752H, RG752S, RG753H, RG753S, RG755S, RG756S, RG757S, and RG858S. In some embodiments, the biodegradable ocular implant of the disclosure comprises at least two PLGA in a ratio of about 99%:about 1% (e.g., about 98%:about 2%, about 97%:about 3%, about 96%:about 4%, about 95%:about 5%, about 94%:about 6%, about 95%:about 5%, about 94%:about 6%, about 93%:about 7%, about 92%:about 8%, about 91%:about 9%, about 90%:about 10%, about 90%:about 10%, about 89%:about 11%, about 88%:about 12%, about 87%:about 13%, about 87%:about 13%, about 86%:about 14%, about 85%:about 15%, about 84%:about 16%, about 83%:about 17%, about 82%:about 18%, about 81%:about 19%, about 80%:about 20%, about 79%:about 21%, about 78%:about 22%, about 77%:about 23%, about 76%:about 24%, about 75%:about 25%, about 74%:about 26%, about 73%:about 27%, about 72%:about 28%, about 71%:about 29%, about 70%:about 30%, about 69%:about 31%, about 68%:about 32%, about 67%:about 33%, about 66%:about 34%, about 65%:about 35%, about 64%:about 36%, about 63%:about 37%, about 62%:about 38%, about 61%:about 39%, about 60%:about 40%, about 59%:about 41%, about 58%:about 42%, about 57%:about 43%, about 56%:about 44%, about 55%:about 45%, about 54%:about 46%, about 53%:about 47%, about 52%:about 48%, about 51%:about 49%, about 50%:about 50%, about 49%:about 51%, about 48%:about 52%, about 47%:about 53%, about 46%:about 54%, about 45%:about 55%, about 44%:about 56%, about 43%:about 57%, about 42%:about 58%, about 41%:about 59%, about 40%:about 60%, about 39%:about 61%, about 38%:about 62%, about 37%:about 63%, about 36%:about 64%, about 35%:about 65%, about 34%:about 66%, about 33%:about 67%, about 32%:about 68%, about 31%:about 69%, about 30%:about 70%, about 29%:about 71%, about 28%:about 72%, about 27%:about 73%, about 26%:about 74%, about 25%:about 75%, about 24%:about 76%, about 23%:about 77%, about 22%:about 78%, about 21%:about 79%, about 20%:about 80%, about 19%:about 81%, about 18%:about 82%, about 17%:about 83%, about 16%:about 84%, about 15%:about 85%, about 14%:about 86%, about 13%:about 87%, about 12%:about 88%, about 11%:about 89%, about 10%, about 90%, about 9%:about 91%, about 8%:about 92%, about 7%:about 93%, about 6%:about 94%, about 5%:about 95%, about 4%:about 96%, about 3%:about 97%, about 2%:about 98%, and about 1%:about 99%). In some embodiments, the biodegradable ocular implant of the disclosure comprises at least two PLGA in a ratio of about 50% to about 75%:about 25% to about 50% (e.g., about 50% to about 70%:about 30% to 50%, about 50% to about 65%:about 35% to about 50%, about 50% to about 60%:about 40% to about 50%, and about 55%:about 45%). In certain embodiments, the biodegradable ocular implant of the disclosure comprises at least two PLGA in a ratio of about 50%:about 50%. In embodiments, the two PLGA are RG503 and RG503H. In embodiments, the two PLGA are RG502 and RG502H. In embodiments, the two PLGA are RG504 and RG504H.

In some embodiments, the biodegradable polymer comprises at least three varying biodegradable polymers. In some embodiments, the biodegradable polymer comprises at least three PLGA, wherein each PLGA is independently selected from the group consisting of RG502, RG502H, RG503, RG503H, RG504, RG504H, RG505, RG653H, RG750S, RG752H, RG752S, RG753H, RG753S, RG755S, RG756S, RG757S, and RG858S. In some embodiments, the biodegradable polymer comprises at least three PLGA in a ratio of about 1% to about 95% (e.g., about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%):about 1% to about 95% (e.g., about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%):about 1% to about 95% (e.g., about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%).

In some embodiments, the biodegradable polymer comprises at least three PLGA in a ratio of about 40%:about 40%:about 20%. In some embodiments, the biodegradable polymer comprises at least three PLGA in a ratio of about 50%:about 10%:about 40%. In some embodiments, the biodegradable polymer comprises at least three PLGA in a ratio of about 10%:about 50%:about 40%. In some embodiments, the biodegradable polymer comprises at least three PLGA in a ratio of about 40%:about 40%:about 20%. In some embodiments, the biodegradable polymer comprises at least three PLGA in a ratio of about 10%:about 50%:about 40%. In some embodiments, the biodegradable polymer comprises at least three PLGA in a ratio of about 20%:about 60%:about 20%. In some embodiments, the biodegradable polymer comprises at least three PLGA in a ratio of about 20%:about 50%:about 30%. In some embodiments, the biodegradable polymer comprises at least three PLGA in a ratio of about 15%:about 50%:about 35%. In some embodiments, the biodegradable polymer comprises at least three PLGA in a ratio of about 15%:about 45%:about 40%. In embodiments, each PLGA is independently selected from the group consisting of RG503, RG503H and RG753S. In embodiments, each PLGA is independently selected from the group consisting of RG502, RG503, and RG753S. In embodiments, each PLGA is independently selected from the group consisting of RG502, RG503, and RG752S. In certain embodiments, each PLGA is independently selected from the group consisting of RG502, RG503, and RG755S. In certain embodiments, each PLGA is independently selected from the group consisting of RG502, RG503, and RG756S.

In some embodiments, the biodegradable polymer comprises at least four varying biodegradable polymers. In some embodiments, the biodegradable polymer comprises at least four PLGA, wherein each PLGA is independently selected from the group consisting of RG502, RG502H, RG503, RG503H, RG504, RG504H, RG505, RG653H, RG750S, RG752H, RG752S, RG753H, RG753S, RG755S, RG756S, RG757S, and RG858S. In certain embodiments, the biodegradable polymer comprises at least four PLGA, wherein each PLGA is independently selected from the group consisting of RG502, RG503, RG753S, RG755S, RG756S, and RG858S. In certain embodiments, the biodegradable polymer comprises at least four PLGA, wherein each PLGA is independently selected from the group consisting of RG502, RG503, RG753S, and RG858S.

In some embodiments, the biodegradable polymer comprises at least four PLGA in a ratio of about 1% to about 95% (e.g., about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%):about 1% to about 95% (e.g., about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%):about 1% to about 95% (e.g., about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%):about 1% to about 95% (e.g., about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%).

In some embodiments, the biodegradable polymer comprises at least four PLGA in a ratio of about 10% to about 30% (e.g., about 10%, about 15%, about 20%, about 25%, and about 30%):about 20% to about 40% (e.g., about 20%, about 25%, about 30%, about 35%, about 40%):about 20% to about 40% (e.g., about 20%, about 25%, about 30%, about 35%, about 40%):about 10% to about 30% (e.g., about 10%, about 15%, about 20%, about 25%, and about 30%). In some embodiments, the biodegradable polymer comprises at least four PLGA in a ratio of about 1% to about 20% (e.g., about 1%, about 5%, about 10%, about 15%, about 20%):about 40% to about 60% (e.g., about 40%, about 45%, about 50%, about 55%, about 60%):about 20% to about 40% (e.g., about 20%, about 25%, about 30%, about 35%, about 40%):about 1% to about 20% (e.g., about 1%, about 5%, about 10%, about 15%, about 20%).

In certain embodiments, the biodegradable polymer comprises at least four PLGA in a ratio of about 20%:about 30%:about 30%:about 20%. In certain embodiments, the biodegradable polymer comprises at least four PLGA in a ratio of about 10%:about 50%:about 30%:about 10%. Each of the four PLGA in the biodegradable polymer may independently selected from the group consisting of RG502, RG503, RG753S, RG755S, RG756S, and RG858S. In some embodiments, each PLGA is independently RG502, RG503, RG753S, or RG858S.

In some embodiments, the biodegradable polymer comprises RG503, RG502 and RG753S in a ratio of about 40 to about 60%:about 5 to about 20%:about 30 to about 50%. In certain embodiments, the biodegradable polymer comprises RG503, RG502 and RG753S in a ratio of about 50%:about 10%:about 40%.

In some embodiments, the biodegradable polymer (e.g., PLGA) biodegrades substantially from about 1 month to about 24 months (e.g., about 2 months to about 24 months, about 5 months to 24 months, about 7 months to about 10 months, about 10 months to about 24 months, about 12 months to about 24 months, about 15 months to about 24 months, about 17 months to about 24 months, about 20 months to about 24 months, and about 22 months to about 24 months). In some embodiments, the biodegradable polymer (e.g., PLGA) biodegrades substantially from about 3 months to about 12 months (e.g., about 4 months to about 12 months, 5 months to about 12 months, about 5 months to about 12 months, about 6 months to about 12 months, about 7 months to about 12 months, about 8 months to about 12 months, about 9 months to about 12 months, about 10 months to about 12 months, and about 11 months to about 12 months). In some embodiments, the biodegradable polymer (e.g., PLGA) biodegrades substantially from about 12 months to about 18 months (e.g., about 13 months to about 18 months, about 14 months to about 18 months, about 15 months to about 18 months, about 16 months to about 18 months, and about 17 months to about 18 months). In some embodiments, the biodegradable polymer (e.g., PLGA) biodegrades substantially from about 3, 4, 5, 6, 7, 8, 9, 10, 11 or 12 months.

Biodegradable Ocular Implant

The biodegradable ocular implant described herein comprises a biodegradable polymer containing a compound incorporated therein. In preferable embodiments, the compound is a compound of Formula I. The biodegradable ocular implant of the present disclosure may treat an ocular disease, comprising contacting an optical tissue in a subject with the biodegradable ocular implant, wherein the ocular disease is selected from the group consisting of glaucoma, diabetic retinopathy (DR), retinal vein occlusion (RVO), and retinopathy of prematurity (ROP), and the compound is present in an amount therapeutically effective for treating the ocular disease.

In various embodiments, the implant has a diameter of about 300 μm to about 400 μm (e.g., about 300 μm, about 325 μm, about 350 μm, about 375 μm, and about 400 μm), and a length of about 4 mm to about 5 mm (e.g., about 4.1 mm, about 4.2 mm, about 4.3 mm, about 4.4 mm, about 4.5 mm, about 4.6 mm, about 4.7 mm, about 4.8 mm, about 4.9 mm, and about 5 mm). In certain embodiments, the implant has a diameter of about 300 μm and a length of about 4 mm. In certain embodiments, the implant has a diameter of about 340 μm and a length of about 4 mm.

In various embodiments, the implant has a total weight of about 250 μg to about 450 μg (e.g., about 250 μg, about 270 μg, about 290 μg, about 310 μg, about 330 μg, about 350 μg, about 370 μg, about 390 μg, about 410 μg, about 430 μg, and about 450 μg). In various embodiments, the implant has a total weight of about 300 μg to about 450 μg. In various embodiments, the implant has a total weight of about 350 μg to about 450 μg. In some embodiments, the implant has a total weight of about 380 μg.

In some embodiments, the biodegradable ocular implant comprises initially at least about 95% to about 99% (e.g., about 95%, about 96%, about 97%, about 98%, and about 99%) of a matrix of the biodegradable polymer and the compound. In some embodiments, the biodegradable ocular implant comprises initially at least 95% of a matrix of the biodegradable polymer and the compound. In some embodiments, the biodegradable ocular implant comprises initially at least about 80% to about 95% (e.g., about 80%, about 81%, about 82%, about 83%, about 84%, about 85%, about 86%, about 87%, about 88%, about 89%, about 90%, about 91%, about 92%, about 93%, about 94%, and about 95%) of a matrix of the biodegradable polymer and the compound.

In certain embodiments, the biodegradable ocular implant comprises about

The rate of therapeutic agent (e.g., a compound of Formula I) release from a intravitreal implant or particle suspension (for example, a biodegradable ocular implant of the present disclosure) may depend on several factors, including but not limited to the surface area of the implant, therapeutic agent content, and water solubility of the therapeutic agent, and speed of polymer degradation.

In some embodiments, less than 40% (e.g., about 40%, about 35%, about 30%, about 25%, about 20%, about 15%, about 10%, and about 5%) of the compound is released from the biodegradable ocular implant when placed in phosphate buffered saline (PBS) in about 1 month. In some embodiments, less than 90% (e.g., about 90%, about 85%, about 80%, about 75%, about 70%, about 65%, about 60%, about 55%, about 50%, about 45%, about 40%, about 35%, about 30%, about 25%, about 20%, about 15%, about 10%, and about 5%) of the compound is released from the biodegradable ocular implant when placed in phosphate buffered saline (PBS) in about 1 month to about 12 months (about 1 month, about 2 months, about 3 months, about 4 months, about 5 months, about 6 months, about 7 months, about 8 months, about 9 months, about 10 months, about 11 months, about 12 months).

In various embodiments, the implant is administered as an intravitreal administration. An intravitreal administration refers to drug administration into the vitreous humor of the eye. In some embodiments, the implant is administered locally to the back of the eye. In some embodiments, the implant is injected into the intravitreal space using a needle and applicator. In some embodiments, the biodegradable ocular implant comprises a dose of the compound (e.g., compound of Formula I) in a range of about 1 μg to about 1 mg (e.g., about 1 μg, about 10 μg, about 25 μg, about 50 μg, about 75 μg, about 100 μg, about 125 μg, about 150 μg, about 175 μg, about 200 μg, about 225 μg, about 250 μg, about 275 µg, about 300 µg, about 325 µg, about 350 µg, about 375 µg, about 400 µg, about 425 µg, about 450 µg, about 475 µg, about 500 µg, about 525 µg, about 550 µg, about 575 µg, about 600 µg, about 625 µg, about 650 µg, about 675 µg, about 700 µg, about 725 µg, about 750 µg, about 775 µg, about 800 µg, about 825 µg, about 850 µg, about 875 µg, about 900 µg, about 925 µg, about 950 µg, and about 975 µg). In some embodiments, the biodegradable ocular implant comprises a dose of the compound (e.g., compound of Formula I) in a range of about 10 µg to about 100 µg. In some embodiments, the biodegradable ocular implant comprises a dose of the compound (e.g., compound of Formula I) in a range of about 500 µg to about 4 mg (e.g., about 1 mg, about 1.5 mg, about 2 mg, about 2.5 mg, about 3 mg, and about 3.5 mg). In some embodiments, the dose is about 150 µg to about 250 µg. In certain embodiments, the dose is about 165 µg to about 220 µg (e.g., about 165 µg, about 170 µg, about 175 µg, about 180 µg, about 185 µg, about 190 µg, about 195 µg, about 200 µg, about 205 µg, about 210 µg, about 215 µg, and about 220 µg). In some embodiments, the dose is about 300 µg to about 500 µg. In some embodiments, the dose is about 300 µg to about 550 µg. In some embodiments, the dose is about 300 µg to about 600 µg. In certain embodiments, the dose is about 330 µg to about 500 µg (e.g., about 330 µg, about 335 µg, about 340 µg, about 345 µg, about 350 µg, about 355 µg, about 360 µg, about 365 µg, about 370 µg, about 375 µg, about 380 µg, about 385 µg, about 390 µg, about 395 µg, about 400 µg, about 405 µg, about 410 µg, about 415 µg, about 420 µg, about 425 µg, about 430 µg, about 435 µg, about 440 µg, about 445 µg, about 450 µg, about 455 µg, about 460 µg, about 465 µg, about 470 µg, about 475 µg, about 480 µg, about 485 µg, about 490 µg, about 495 µg, and about 500 µg). In some embodiments, the dose is about 200 µg to about 400 µg (e.g., about 200 µg, about 210 µg, about 220 µg, about 230 µg, about 240 µg, about 250 µg, about 260 µg, about 270 µg, about 280 µg, about 290 µg, about 300 µg, about 310 µg, about 320 µg, about 330 µg, about 340 µg, about 350 µg, about 360 µg, about 370 µg, about 380 µg, about 390 µg, about 400 µg). In some embodiments, the dose is about 175 µg.

In some embodiments, the biodegradable ocular implant is a sterile biodegradable ocular implant. As used herein, "sterile" refers to the composition meeting the requirements of sterility enforced by medicine regulatory authorities, such as the MCA in the UK or the FDA in the US. Tests are included in current versions of the compendia, such as the British Pharmacopoeia and the US Pharmacopoeia. In some embodiments, the biodegradable ocular implant is a substantially pure biodegradable ocular implant. In some embodiments, the biodegradable ocular implant is a medical-grade biodegradable ocular implant. In some embodiments, the biodegradable ocular implant is administered into the intravitreal space every 3 to 12 months.

In some embodiments, provided herein is a biodegradable ocular implant comprising: a biodegradable polymer containing a compound incorporated therein; wherein the compound is a compound of Formula I or a pharmaceutically acceptable salt thereof, wherein the concentration of the compound in the biodegradable polymer is about 45% w/w; and the biodegradable polymer comprises RG503, RG502 and RG753S in a ratio of about 50%:about 10%:about 40%.

In some certain embodiments, provided herein is a biodegradable ocular implant comprising: a biodegradable polymer containing a compound incorporated therein; wherein the compound is a compound of Formula I or a pharmaceutically acceptable salt thereof, wherein the concentration of the compound in the biodegradable polymer is about 45% w/w; and the biodegradable polymer comprises RG503, RG502 and RG753S in a ratio of about 20%:about 20%:about 60%.

Method of Making

A method of making a biodegradable ocular implant described herein comprises subjecting a biodegradable polymer containing a compound via solvent casting, injection molding, or extrusion, wherein the compound is a compound of Formula I:

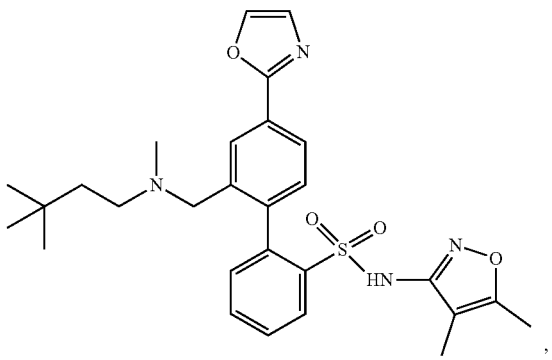

(I)

or a pharmaceutically acceptable salt thereof.

Prior to implant fabrication blends of the polymer matrix and therapeutic agent may be dissolved and mixed with solvent to produce homogeneously dispersed therapeutic agent through the body of the implant. Prepared blends may each contain a different ratio of multiple, e.g., three, different PLGA polymers. The PLGA polymers used to produce the pharmaceutical compositions of the present invention may include, but are not limited to, RESOMER® RG502, RG503, RG752S RG753S, and 65/35 PLA/PLG, all of which are commercially available.

The following is an exemplary procedure used to prepare the compositions of the present invention: For example the polymers, in a particular ratio, are dissolved in an organic solvent, such as methylene chloride. The therapeutic agent (such as Edonentan) are then added to the polymer solution and dissolved. The methylene chloride is then evaporated in a polytetrafluoroethylene (PTFE) dish at room temperature. After the methylene chloride is evaporated, a thin film of homogeneous material remains. In an embodiment, the thin films range from 200 µm to 300 µm in thickness.

The remaining homogenous film is then milled to a powder using a cryogenic mill. Small portions of the film are added to stainless steel cryogenic milling vessels with 2 to 3 appropriately sized grinding balls and precooled using liquid nitrogen for 2 to 3 minutes at 5 Hz. The material is then milled for 1 minute from 20 Hz to 25 Hz with 1 minute of rest at 5 Hz. This milling/rest cycle is repeated from 2 to 5 times. The resulting material is a coarse to fine powder of homogenous material.

The implants of the present invention may be prepared, in an embodiment, using the homogenous material described above. In an embodiment, the implants are formed by injection molding. Injection molding can, for example, be performed by a suitable injection molder, such as a modified Haake MiniJet (ThermoFisher Scientific). The following is an exemplary procedure used to prepare the implants of the present invention.

The homogeneous powder is loaded and injected into a mold consisting of channels of an appropriate size, such as 300 μm×12 mm. The powder is loaded into a barrel leading into the mold and the mold placed under vacuum. The mold temperature is held from 15° C. to 75° C. The cylinder, surrounding the powder loaded barrel, is held from 145° C. to 220° C. for 10 to 15 minutes to melt the powder blend. The injection is performed using an injection pressure of 220 bar to 330 bar holding for 2 to 10 minutes. A post injection pressure is held at 50 bar from 2 to 10 minutes. The mold is then cooled down to 15 to 23° C. before removing the mold from the injection molder. The molded fibers are then removed from the mold and then cut into implants with a target weight and length. In some embodiments, the implants are 4 mm in length and contain about 165 μg to about 220 μg of active ingredient, such as Edonentan.

The implants of the present invention may be prepared, in an embodiment, using the homogenous material described above. In an embodiment, the implants are formed by extrusion for example, hot melt extrusion. Hot melt extrusion can be performed using ThermoFisher Pharma mini HME Micro Compounder, ThermoFisher FP-Pharma-11-Twin-230×100, ThermoFisher Pharma 11 Twin-Screw Extruder, ThermoFisher FP-Pharma 230×100, ThermoFisher Pharma 16 Twin-Screw Extruder, or Barrell Engineering Micro Syringe Type Extruder.

Crystalline Forms

In another aspect, the biodegradable ocular implants described herein and methods of use thereof comprise a biodegradable polymer containing a solid form of a compound of Formula I.

In certain embodiments, the solid form of the compound of Formula I:

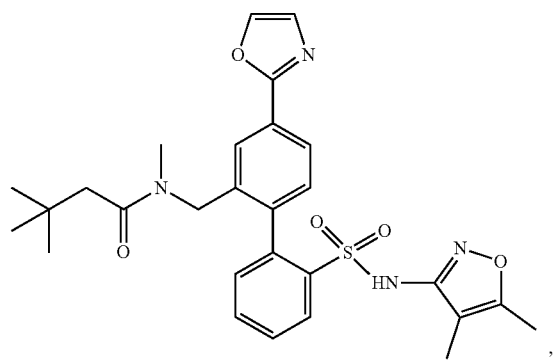

(I)

is an anhydrous crystalline form (Form 4), having an X-ray powder diffraction pattern comprising at least three characterization peaks, in terms of 2θ, selected from peaks at 5.6±0.2°, 11.4±0.2°, 17.7±0.2°, 19.3±0.2°, 21.1±0.2°, and 21.9±0.2°.

In some embodiments of the solid form, the anhydrous crystalline Form 4 has the following X-ray powder diffraction pattern expressed in terms of diffraction angles (2θ): 5.6±0.2°, 11.4±0.2°, 17.7±0.2°, 19.3±0.2°, and 21.9±0.2°. In some embodiments of the solid form, the anhydrous crystalline Form 4 has the following X-ray powder diffraction pattern expressed in terms of diffraction angles (2θ): 11.4±0.2°, 17.7±0.2°, and 19.3±0.2°. In some embodiments of the solid form, the anhydrous crystalline Form 4 shows a T. of about 163° C. by DSC analysis. In some embodiments of the solid form, the anhydrous crystalline Form 4 has the following X-ray powder diffraction pattern expressed in terms of diffraction angles (2θ): 5.6±0.2°, 11.4±0.2°, 17.7±0.2°, 19.3±0.2°, and 21.9±0.2°. In some embodiments of the solid form, the anhydrous crystalline Form 4 has the following X-ray powder diffraction pattern expressed in terms of diffraction angles (2θ): 11.4±0.2°, 17.7±0.2°, and 19.3±0.2°. In some embodiments of the solid form, the anhydrous crystalline Form 4 shows a T. of about 163° C. by DSC analysis.

In some embodiments, said compound is 90% by weight or more in crystalline Form 4 based on the total weight of the compound present in the composition. In some embodiments, the compound of Formula I is 95% by weight or more in crystalline Form 4 based on the total weight of the compound present in the composition. In some embodiments, the compound of Formula I is 96% by weight or more in crystalline Form 4 based on the total weight of the compound present in the composition. In some embodiments, the compound of Formula I is 97% by weight or more in crystalline Form 4 based on the total weight of the compound present in the composition. In some embodiments, the compound of Formula I is 98% by weight or more in crystalline Form 4 based on the total weight of the compound present in the composition. In some embodiments, the compound of Formula I is 99% by weight or more in crystalline Form 4 based on the total weight of the compound present in the composition.

In certain embodiments, the compound of Formula I is an anhydrous crystalline form (Form 1), wherein the anhydrous crystalline Form 1 has an X-ray powder diffraction pattern comprising at least three characterization peaks, in terms of 2θ, selected from peaks at 6.3±0.2°, 7.5±0.2°, 11.7±0.2°, 15.1±0.2°, and 17.3±0.2°; and said compound is 90% by weight or more in crystalline Form 1 based on the total weight of the compound present in the composition.

In certain embodiments, the compound of Formula I is a monohydrate crystalline form (Form 2), wherein the monohydrate crystalline Form 2 has an X-ray powder diffraction pattern comprising at least three characterization peaks, in terms of 2θ, selected from peaks at 9.6±0.2°, 10.4±0.2°, 19.6±0.2°, 19.7±0.2°, 22.0±0.2°, 22.9±0.2°, and 23.7±0.2°; and said compound is 90% by weight or more in crystalline Form 2 based on the total weight of the compound present in the composition;

In certain embodiments, the compound of Formula I is an anhydrous crystalline (Form 3), wherein the anhydrous crystalline Form 3 has an X-ray powder diffraction pattern comprising at least three characterization peaks, in terms of 2θ, selected from peaks at 7.8±0.2°, 9.0±0.2°, 11.6±0.2°, 15.8±0.2°, and 19.1±0.2°; and said compound is 90% by weight or more in crystalline Form 3 based on the total weight of the compound present in the composition.

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern.

Hydrate forms of crystalline Edonentan are contemplated, e.g., Edonentan $(H_2O)_m$, where m is a fractional or whole number between about 0 and about 4 inclusive. For example, contemplated herein are anhydrate or monohydrate forms of crystalline Edonentan. In an embodiment, a disclosed crystalline form of Edonentan may have a water level of about 1 to 10% by weight (e.g., 3 to 9% or 5 to 8% by weight).

Ocular Diseases

The methods of the present disclosure include the use of biodegradable ocular implants comprising Edonentan described above in the treatment and amelioration of an ocular disease selected from glaucoma, diabetic retinopathy (DR), retinal vein occlusion (RVO), and retinopathy of prematurity (ROP), which are described below.

Glaucoma

In the treatment of glaucoma using compositions comprising Edonentan described herein, a "therapeutically effective amount" can be determined by assessing an improvement in retinal blood flow (RBF) over what could be achieved by the standard of care (lowering of intra-ocular pressure (IOP)). For a glaucoma indication, the improvement in blood flow in the healthy rabbit ocular model can be used as predictive of pharmacodynamic response (PD) in humans. Rabbits are commonly used to assess ocular PK/PD relationship for compounds targeting human ocular diseases due to the anatomic and functional similarities of the rabbit and human eye. Previously, intravitreal administration of ET-1 into the rabbit eye has been shown to induce significant vasoconstriction and optic nerve damage (Sasaoka M. et al, Exp Eye Res 2006; Sugiyama T. et al, Arch Ophthalmol 2009). Efficacy in this model is benchmarked to the reversal of perfusion impairment induced by intravitreal ET-1 administration at a concentration equivalent to the levels observed in human glaucoma patients' plasma and aqueous humor (Li S. et al, Journal of Ophthalmology 2016).

Other examples of relevant animal glaucoma models are Morrison's rat model of acutely elevated IOP and the laser-induced non-human primate (NHP) glaucoma model. Glaucoma in Morrison's rat model is induced by sustained elevation of IOP through hypertonic saline administration via episcleral veins. In the laser-induced NHP glaucoma model, after sustained elevation of IOP, optic nerve head blood flow has been shown to be reduced (Wang L. et al, Invest Ophthalmol Vis Sci 2012). Furthermore, the reduction in optic nerve head blood flow has been shown to correlate with long-term structural changes in the optic nerve (Cull G. et al, Invest Ophthalmol Vis Sci 2013).

Efficacy in the above-described glaucoma models is defined as reduction in IOP, improvement in optic nerve head or retinal blood flow from baseline, prevention or slowing of the progression of structural neurodegenerative changes such as retinal nerve fiber layer thickness as measured by optical coherence tomography (OCT) or retinal ganglion cell counts on flat mount as well as functional changes such as electroretinography (ERG) or contrast sensitivity after treatment with Edonentan.

It is believed that the effect of compositions comprising Edonentan on retinal blood flow can be assessed by the blood vessel radius (r) in Poiseuille's Law. An increase in (r) with an endothelin antagonist, would induce a more pronounced increase in blood flow than what can be achieved by an increase in perfusion pressure through IOP reduction:

Blood flow=(perfusion pressure×$\pi r^4$)/($8\eta l$)

where l: blood vessel length
r: blood vessel radius
$\eta$: blood viscosity
perfusion pressure: mean arterial pressure—IOP Furthermore, compositions comprising Edonentan may reduce IOP and/or prevent RGC death through mechanisms independent of improvement in retinal/optic nerve head tissue perfusion. Accordingly, by using certain specific Edonentan, one (r) or more (IOP) of the above parameters can be altered to improve the RBF, thereby achieving therapeutic efficacy in treating glaucoma.

In some embodiments, the glaucoma patients are started on treatment as soon as they are diagnosed. In some embodiments, a biodegradable ocular implant comprising a compound of Formula I (Edonentan) is administered locally to the back of the eye using (e.g., using an intravitreal biodegradable ocular implant), with a frequency of every 3 to 12 months (e.g., every 4 to 12 months, every 5 to 12 months, every 6 to 12 months, every 7 to 12 months, every 8 to 12 months, every 9 to 12 months, every 10 to 12 months, every 11 to 12 months, every 3 to 4 months, every 3 to 5 months, every 3 to 6 months, every 3 to 7 months, every 3 to 8 months, every 3 to 9 months, every 3 to 10 months, or every 3 to 11 months).

In some embodiments, the biodegradable ocular implant for treating glaucoma in a subject in need thereof comprises a biodegradable polymer (e.g., PLGA) that biodegrades substantially from about 1 month to about 24 months (e.g., about 2 months to about 24 months, about 5 months to 24 months, about 7 months to about 10 months, about 10 months to about 24 months, about 12 months to about 24 months, about 15 months to about 24 months, about 17 months to about 24 months, about 20 months to about 24 months, and about 22 months to about 24 months). In some embodiments, the biodegradable polymer (e.g., PLGA) biodegrades substantially from about 3 months to about 12 months (e.g., about 4 months to about 12 months, 5 months to about 12 months, about 5 months to about 12 months, about 6 months to about 12 months, about 7 months to about 12 months, about 8 months to about 12 months, about 9 months to about 12 months, about 10 months to about 12 months, and about 11 months to about 12 months). In some embodiments, the biodegradable polymer (e.g., PLGA) biodegrades substantially from about 12 months to about 18 months (e.g., about 13 months to about 18 months, about 14 months to about 18 months, about 15 months to about 18 months, about 16 months to about 18 months, about 17 months to about 18 months). In some embodiments, the biodegradable polymer (e.g., PLGA) biodegrades substantially in about 3, 4, 5, 6, 7, 8, 9, 10, 11 or 12 months.

Diabetic Retinopathy (DR)

Diabetes can cause serious late complications which are classified as microangiopathic (retinopathy, neuropathy, and diabetic nephropathy) and macroangiopathic (cardiovascular disease). Diabetic retinopathy is the result of damage to the small blood vessels and neurons of the retina. The earliest changes leading to diabetic retinopathy include narrowing of the retinal arteries associated with reduced retinal blood flow; dysfunction of the neurons of the inner retina, followed in later stages by changes in the function of the outer retina, associated with subtle changes in visual function; dysfunction of the blood-retinal barrier, which protects the retina from many substances in the blood (including toxins and immune cells), leading to the leakage of blood constituents into the retinal neuropile. Later, the basement membrane of the retinal blood vessels thickens, capillaries degenerate and lose cells, particularly pericytes and vascular smooth muscle cells. This leads to loss of blood flow and progressive ischemia, and microscopic aneurysms which appear as balloon-like structures jutting out from the capillary walls, which recruit inflammatory cells; and lead to advanced dysfunction and degeneration of the neurons and glial cells of the retina.

Ischemia and oxidant injury observed in DR compromises blood flow and tissue ischemia which we have discovered can be reversed by compositions comprising Edonentan. For DR indication, the improvement in retinal perfusion is anticipated to reduce hypoxia and suppress vascular endothelial growth factor (VEGF) upregulation with a resultant benefit of slowing vascular proliferative changes, neovascularization and/or macular edema complications.

As a surrogate model for the ischemic retinopathy changes observed in DR, a preclinical mouse model of retinopathy of prematurity (ROP) can be used. Oxygen-induced retinopathy in the mouse is a reproducible and quantifiable proliferative retinal neovascularization model suitable for examining pathogenesis and therapeutic intervention for retinal neovascularization in ROP and other vasculopathologies including DR. The model is induced by exposure of one-week-old C57BL/6J mice to 75% oxygen for 5 days and then to room air as previously described (Smith L E H et al., Invest Ophthalmol Vis Sci 1994). Efficacy in this preclinical model of ROP can be assessed by studying retinal hypoxia and neovascularization. The current standard of care in DR includes anti-VEGF therapies which only address advanced vascular complications of disease.

In some embodiments, the patients with DR are started on this treatment during the non-proliferative stages of the disease. In some embodiments, a biodegradable ocular implant comprising a compound of Formula I (Edonentan) is administered locally to the back of the eye (e.g., using an intravitreal biodegradable ocular implant), with a frequency of every 3 to 12 months (e.g., every 4 to 12 months, every 5 to 12 months, every 6 to 12 months, every 7 to 12 months, every 8 to 12 months, every 9 to 12 months, every 10 to 12 months, every 11 to 12 months, every 3 to 4 months, every 3 to 5 months, every 3 to 6 months, every 3 to 7 months, every 3 to 8 months, every 3 to 9 months, every 3 to 10 months, or every 3 to 11 months).

In some embodiments, the biodegradable ocular implant for treating DR in a subject in need thereof comprises a biodegradable polymer (e.g., PLGA) that biodegrades substantially from about 1 month to about 24 months (e.g., about 2 months to about 24 months, about 5 months to 24 months, about 7 months to about 10 months, about 10 months to about 24 months, about 12 months to about 24 months, about 15 months to about 24 months, about 17 months to about 24 months, about 20 months to about 24 months, and about 22 months to about 24 months). In some embodiments, the biodegradable polymer (e.g., PLGA) biodegrades substantially from about 3 months to about 12 months (e.g., about 4 months to about 12 months, 5 months to about 12 months, about 5 months to about 12 months, about 6 months to about 12 months, about 7 months to about 12 months, about 8 months to about 12 months, about 9 months to about 12 months, about 10 months to about 12 months, and about 11 months to about 12 months). In some embodiments, the biodegradable polymer (e.g., PLGA) biodegrades substantially from about 12 months to about 18 months (e.g., about 13 months to about 18 months, about 14 months to about 18 months, about 15 months to about 18 months, about 16 months to about 18 months, about 17 months to about 18 months). In some embodiments, the biodegradable polymer (e.g., PLGA) biodegrades substantially in about 3, 4, 5, 6, 7, 8, 9, 10, 11 or 12 months.

Retinal Vein Occlusion (RVO)

Retinal vein occlusion (RVO), a vascular disorder of the retina, is currently treated with intravitreal injection of anti-VEGF drugs to inhibit the growth factor that causes macular edema and corticosteroids to combat the inflammatory components which lead to edema. It is highly desirable to use compositions comprising Edonentan for treating RVO by improving tissue perfusion and reducing inflammation while avoiding the unwanted effects of systemic immunosuppression and/or local adverse effects of steroids.

RVO is currently treated with intravitreal steroids and anti-VEGF agents. We hypothesize that improving perfusion of existing vessels will reduce the degree of macular edema and VEGF upregulation and the downstream maladaptive changes that manifests as RVO. To test efficacy, a preclinical mouse model of ischemic retinopathy can be used. Oxygen-induced retinopathy in the mouse is a reproducible and quantifiable proliferative retinal neovascularization model suitable for examining pathogenesis and therapeutic intervention for retinal neovascularization in many ischemic retinopathies including RVO. The model is induced by exposure of one-week-old C57BL/6J mice to 75% oxygen for 5 days and then to room air as previously described (Smith L E H et al., Invest Ophthalmol Vis Sci 1994). The efficacy in this preclinical model of ischemic retinopathy can be assessed by studying retinal hypoxia and neovascularization. A "therapeutically effective amount" of a composition comprising an Edonentan described herein can be additive to the current standard of care by improving tissue perfusion and reducing inflammation mediated by ET-1 while avoiding the unwanted effects of local steroids. In some embodiments of treating RVO, the biodegradable ocular implant comprising a compound of Formula I (Edonentan) is administered locally to the back of the eye using an intravitreal biodegradable ocular implant. The frequency of administration will vary based on a patient's disease course and response to therapy.

In some embodiments, a biodegradable ocular implant comprising a compound of Formula I (Edonentan) is administered locally to the back of the eye (e.g., using an intravitreal biodegradable ocular implant), with a frequency of every 3 to 12 months (e.g., every 4 to 12 months, every 5 to 12 months, every 6 to 12 months, every 7 to 12 months, every 8 to 12 months, every 9 to 12 months, every 10 to 12 months, every 11 to 12 months, every 3 to 4 months, every 3 to 5 months, every 3 to 6 months, every 3 to 7 months, every 3 to 8 months, every 3 to 9 months, every 3 to 10 months, or every 3 to 11 months).

In some embodiments, the biodegradable ocular implant for treating RVO in a subject in need thereof comprises a biodegradable polymer (e.g., PLGA) that biodegrades substantially from about 1 month to about 24 months (e.g., about 2 months to about 24 months, about 5 months to 24 months, about 7 months to about 10 months, about 10 months to about 24 months, about 12 months to about 24 months, about 15 months to about 24 months, about 17 months to about 24 months, about 20 months to about 24 months, and about 22 months to about 24 months). In some embodiments, the biodegradable polymer (e.g., PLGA) biodegrades substantially from about 3 months to about 12 months (e.g., about 4 months to about 12 months, 5 months to about 12 months, about 5 months to about 12 months, about 6 months to about 12 months, about 7 months to about 12 months, about 8 months to about 12 months, about 9 months to about 12 months, about 10 months to about 12 months, and about 11 months to about 12 months). In some embodiments, the biodegradable polymer (e.g., PLGA) biodegrades substantially from about 12 months to about 18 months (e.g., about 13 months to about 18 months, about 14 months to about 18 months, about 15 months to about 18 months, about 16 months to about 18 months, about 17 months to about 18 months). In some embodiments, the biodegradable polymer (e.g., PLGA) biodegrades substantially in about 3, 4, 5, 6, 7, 8, 9, 10, 11 or 12 months.

Retinopathy of Prematurity (ROP)

Retinopathy of prematurity (ROP) is a retinal vasoproliferative disease that affects premature infants. ROP continues to be a major preventable cause of blindness and visual handicaps globally. With improved perinatal care, improved survival of moderately preterm infants, and limited resources for oxygen delivery and monitoring, more mature preterm infants are developing severe ROP in developing countries.

The pathophysiology of ROP is characterized by two phases. Phase I ROP is due to vaso-obliteration beginning immediately after birth secondary to a marked decrease in vascular endothelial growth factor (VEGF) and insulin-like growth factor-1 (IGF-1). Phase II begins around 33 weeks' postmenstrual age (PMA). During this phase, VEGF levels increase, especially if there is retinal hypoxia with increasing retinal metabolism and demand for oxygen leading to abnormal vasoproliferation. For advanced stages of ROP, laser ablation of avascular retina, early treatment of ROP (ETROP) protocol, intravitreal injection of anti-VEGF antibodies (e.g. bevacizumab) and vitrectomy are used to protect central vision and prevent retinal detachment. Long-term complications such as refractory errors, recurrence of ROP and risk of retinal detachment require continued follow-up with an ophthalmologist through adolescence and beyond.

ROP is induced by severe ischemia due to underdevelopment of retinal vessels secondary to premature birth. Therefore, as an aspect of the disclosure, we believe that improving perfusion of existing vessels with compositions comprising Edonentan will reduce the degree of ischemia and VEGF upregulation and the downstream maladaptive changes that manifests as ROP. To test efficacy, a preclinical mouse model of ROP can be used. Oxygen-induced retinopathy in the mouse is a reproducible and quantifiable proliferative retinal neovascularization model suitable for examining pathogenesis and therapeutic intervention for retinal neovascularization in ROP. The model is induced by exposure of one-week-old C57BL/6J mice to 75% oxygen for 5 days and then to room air as previously described (Smith L E H et al., Invest Ophthalmol Vis Sci 1994). The efficacy in this preclinical model of ROP can be assessed by studying retinal hypoxia and neovascularization. A "therapeutically effective amount" of a composition comprising an Edonentan, as described herein will be additive to the current standard of care by improving tissue perfusion and reducing pathologic neovascularization induced by VEGF. In some embodiments, the medication is administered locally to the back of the eye using an intravitreal biodegradable ocular implant with a frequency of every 4 to 6 weeks as needed based on patient's disease course and response to therapy. For example, the intravitreal biodegradable ocular implant is administered locally to the back of the eye using an intravitreal injection with a frequency of every 5 weeks as needed based on patient's disease course and response to therapy.

In some embodiments, the patients with ROP are started on this treatment during the non-proliferative stages of the disease. In some embodiments, a biodegradable ocular implant comprising a compound of Formula I (Edonentan) is administered locally to the back of the eye using (e.g., an intravitreal biodegradable ocular implant), with a frequency of every 3 to 12 months (e.g., every 4 to 12 months, every 5 to 12 months, every 6 to 12 months, every 7 to 12 months, every 8 to 12 months, every 9 to 12 months, every 10 to 12 months, every 11 to 12 months, every 3 to 4 months, every 3 to 5 months, every 3 to 6 months, every 3 to 7 months, every 3 to 8 months, every 3 to 9 months, every 3 to 10 months, or every 3 to 11 months).

In some embodiments, the biodegradable ocular implant for treating ROP in a subject in need thereof comprises a biodegradable polymer (e.g., PLGA) that biodegrades substantially from about 1 month to about 24 months (e.g., about 2 months to about 24 months, about 5 months to 24 months, about 7 months to about 10 months, about 10 months to about 24 months, about 12 months to about 24 months, about 15 months to about 24 months, about 17 months to about 24 months, about 20 months to about 24 months, and about 22 months to about 24 months). In some embodiments, the biodegradable polymer (e.g., PLGA) biodegrades substantially from about 3 months to about 12 months (e.g., about 4 months to about 12 months, 5 months to about 12 months, about 5 months to about 12 months, about 6 months to about 12 months, about 7 months to about 12 months, about 8 months to about 12 months, about 9 months to about 12 months, about 10 months to about 12 months, and about 11 months to about 12 months). In some embodiments, the biodegradable polymer (e.g., PLGA) biodegrades substantially from about 12 months to about 18 months (e.g., about 13 months to about 18 months, about 14 months to about 18 months, about 15 months to about 18 months, about 16 months to about 18 months, about 17 months to about 18 months). In some embodiments, the biodegradable polymer (e.g., PLGA) biodegrades substantially in about 3, 4, 5, 6, 7, 8, 9, 10, 11 or 12 months.

In various embodiments, the biodegradable ocular implant for treating an ocular disease described herein releases at least 10% of Edonentan after 14 days. In some embodiments, the implant releases about 16% of Edonentan after 14 days. In various embodiments, the biodegradable ocular implant for treating an ocular disease described herein releases at least 25% of Edonentan after 28 days. In some embodiments, the implant releases about 30% of Edonentan after 28 days. In various embodiments, the biodegradable ocular implant for treating an ocular disease described herein releases at least 40% of Edonentan after 56 days. In some embodiments, the implant releases about 48% of Edonentan after 56 days. In various embodiments, the biodegradable ocular implant for treating an ocular disease described herein releases at least 90% of Edonentan after 84 days. In some embodiments, the implant releases about 100% of Edonentan after 84 days.

Pharmaceutical Compositions

Some embodiments described herein relates to a pharmaceutical composition, that can include a therapeutically effective amount of an Edonentan, described herein, or a pharmaceutically acceptable salt thereof, and a pharmaceutically acceptable carrier, diluent, excipient or combination thereof.

The term "pharmaceutical composition" refers to a mixture of one or both compounds disclosed herein with other chemical components, such as diluents or carriers. The pharmaceutical composition facilitates administration of the compound to an organism. Pharmaceutical compositions will generally be tailored to the specific intended route of administration.

Some pharmaceutical compositions involve preparing a pharmaceutically acceptable salt. Pharmaceutically acceptable salts include salts of acidic or basic groups present in compounds of the disclosure. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the disclosure can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts, see Berge et al., 66 J. PHARM. SCI., 1-19 (1977).

The term "pharmaceutically acceptable" defines a carrier, diluent, excipient, salt or composition that is safe and effective for its intended use and possesses the desired biological and pharmacological activity.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability, retarded dissolution etc., to the composition. A "diluent" is a type of excipient.

Definitions

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the term "effective amount" refers to the amount of a compound sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the disclosure can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). "Modulation" includes antagonism (e.g., inhibition), agonism, partial antagonism and/or partial agonism.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

"Therapeutically effective amount" includes an amount of a compound of the disclosure that is effective when administered alone or in combination to treat the desired condition or disorder. "Therapeutically effective amount" includes an amount of the combination of compounds claimed that is effective to treat the desired condition or disorder. The combination of compounds can be additive and is preferably a synergistic combination. Synergy, as described, for example, by Chou and Talalay, Adv. Enzyme Regul. 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower incidence of adverse side effects and/or toxicity, increased efficacy, or some other beneficial effect of the combination compared with the individual components.

As used herein, the term "substantially" refers to the complete or nearly complete extent or degree of an action, characteristic, property, state, structure, or result. For example, a polymer that is "substantially" biodegraded would mean that the object is either completely biodegraded or nearly completely biodegraded.

EXAMPLES

In order that the disclosure described herein may be more fully understood, the following examples are set forth. The synthetic and biological examples described in this application are offered to illustrate the compounds, pharmaceutical compositions, and methods provided herein and are not to be construed in any way as limiting their scope.

Abbreviations: w/w: weight-by-weight; HPLC: high-performance liquid chromatography; PBS: phosphate buffer saline; rpm: revolutions per minute; DB: Dutch-belted; DME: diabetic macular edema; DR: diabetic retinopathy; ERG: electroretinogram; GLP: good laboratory practice; IOP: intraocular pressure; IVT: intravitreal; LC-MS: liquid chromatograph mass spectrometer; MS: mass spectrometer; NPDR: non-proliferative diabetic retinopathy; OCT: optical coherence tomography; PDR: proliferative diabetic retinopathy; PLGA: poly(D,L-lactide-co-glycolide); RPE: retinal pigment epithelium; TK: thymidine kinase; UPLC: ultra-performance liquid chromatography.

Example 1. Preparation and Testing of Exemplary Formulation Punch Disks

Small disks of polymer matrix incorporating Edonentan were prepared for elution rate assessment. The polymers, in particular weight ratios such as 50% RG503 and 50% RG503H (50/50 RG503/RG503H) as shown in Table 1, were dissolved in methylene chloride. Edonentan, at 30% w/w with respect to the total weight of the polymers and Edonentan, was then added to the polymer solution and dissolved. The methylene chloride solution was then evaporated in a polytetrafluoroethylene (PTFE) dish at room temperature for 72 to 120 hours. After the methylene chloride was removed, a thin film of homogeneous mixture of polymer and Edonentan remained. Disks were prepared by using a biopsy punch to cut a disk of 2 mm in diameter out of each film resulting in disks weighing from 900 µg up to 1500 µg resulting in drug load from 270 µg up to 450 µg per disk.

Figure 2:
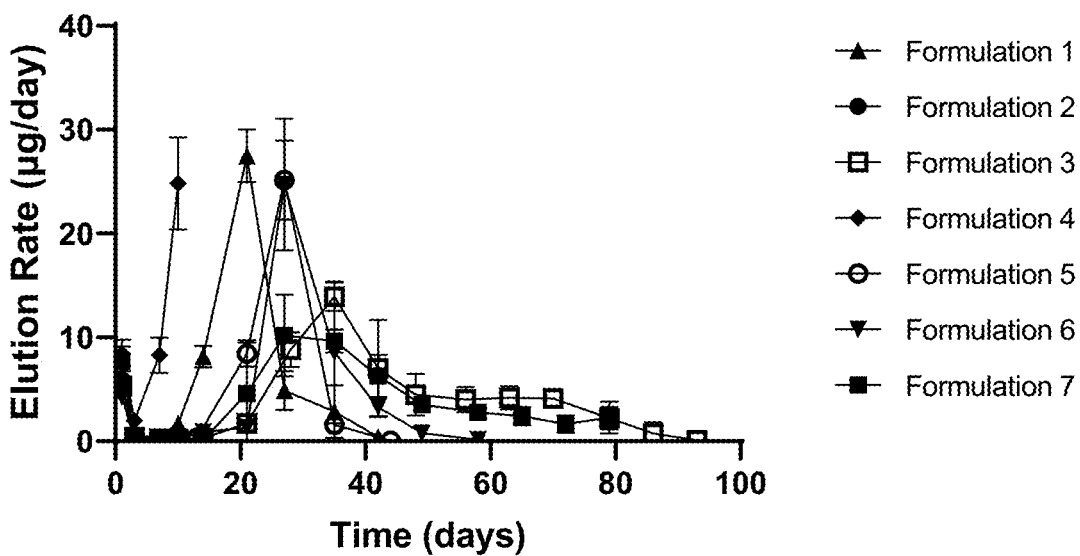
FIG. 2 depicts elution rate profiles of Edonentan in disk punches of exemplary formulations each containing a polymer matrix incorporating Edonentan. The in vitro release results show that for each polymer matrix there is a peak Edonentan release from 10 to 35 days followed by a decrease in elution rate, with a sustained steady-state release for some matrices as determined by HPLC.

For in vitro drug release testing, three film disks per each formulation were cut from films and incubated in 3 mL of PBS pH 7.4 in a shaking incubator set at 37° C. and 50 rpm. The drug release was sampled at designated time points and the released Edonentan content as a function of time was analyzed by an HPLC assay, as shown in FIG. 1. Corresponding elution rates of the Edonentan from the disks as a function of time are provided in FIG. 2. Drug release samples were analyzed by reversed phase chromatography using an Agilent Polaris Amide-C18 column at 40° C. and mobile phases consisting of water and acetonitrile modified with trifluoroacetic acid. Quantitation was performed using an external standard with detection at 275 nm. The release medium was completely replaced with fresh medium during each sampling time point.

Example 2. Preparation and Testing of Exemplary Implants

Using the procedure to produce homogeneous films in Example 1, additional formulations comprising various polymer and drug ratios are shown in Table 2. The formulations were either evaporated at room temperature for 72-120 hours, as described in Example 1, or dried under vacuum at 25° C. and 20 mbar for 24 hours. The films were then milled to a powder using a cryogenic mill. Small portions of the film were added to stainless steel cryogenic milling vessels with 2 to 3 appropriately sized grinding balls and precooled using liquid nitrogen for 2 or 3 minutes at 5 Hz. The material was then milled for 1 minute from 20 Hz to 25 Hz with 1 minute of rest at 5 Hz. This milling/rest cycle was repeated from 2 to 5 times. The resulting material was coarse to fine powder of homogenous material.

Implants were formed by injection molding with a modified Haake MiniJet (ThermoFisher Scientific). The homogeneous powder was loaded and injected into a mold consisting of channels of an appropriate size, such as 300 µm×12 mm or 325 µm×12 mm. The powder was loaded into a barrel leading into the mold and the mold placed under vacuum. The mold temperature was held at 15-25° C. The cylinder, surrounding the powder loaded barrel, was held from 145° C. to 165° C. for 12 to 15 minutes to melt the powder blend. The injection was performed using an injection pressure of 230 bar to 320 bar holding for 2 to 5 minutes. A post injection pressure was held at 50 bar from 2 to 5 minutes. The mold was then cooled to 15 to 23° C. before removing the mold from the injection molder. The molded fibers were then removed from the mold, and they were then cut into 4-mm implants containing 165 µg to 220 µg of Edonentan per implant.

Implants of select formulations were also formed by ram extrusion using a modified Barrell Micro Extruder (Barrell Engineering). The homogeneous powder was loaded into a 3 mm barrel and extruded through a 0.30 µm die maintaining a temperature of 68° C. to 80° C. and a flow rate of 5 µL/min to 6 µl/min. Extruded filaments were then cut into 4-mm implants containing 165 µg to 220 µg of Edonentan per implant. Resulting implants have similar performance characteristics as those produced with injection molding.

Figure 3:
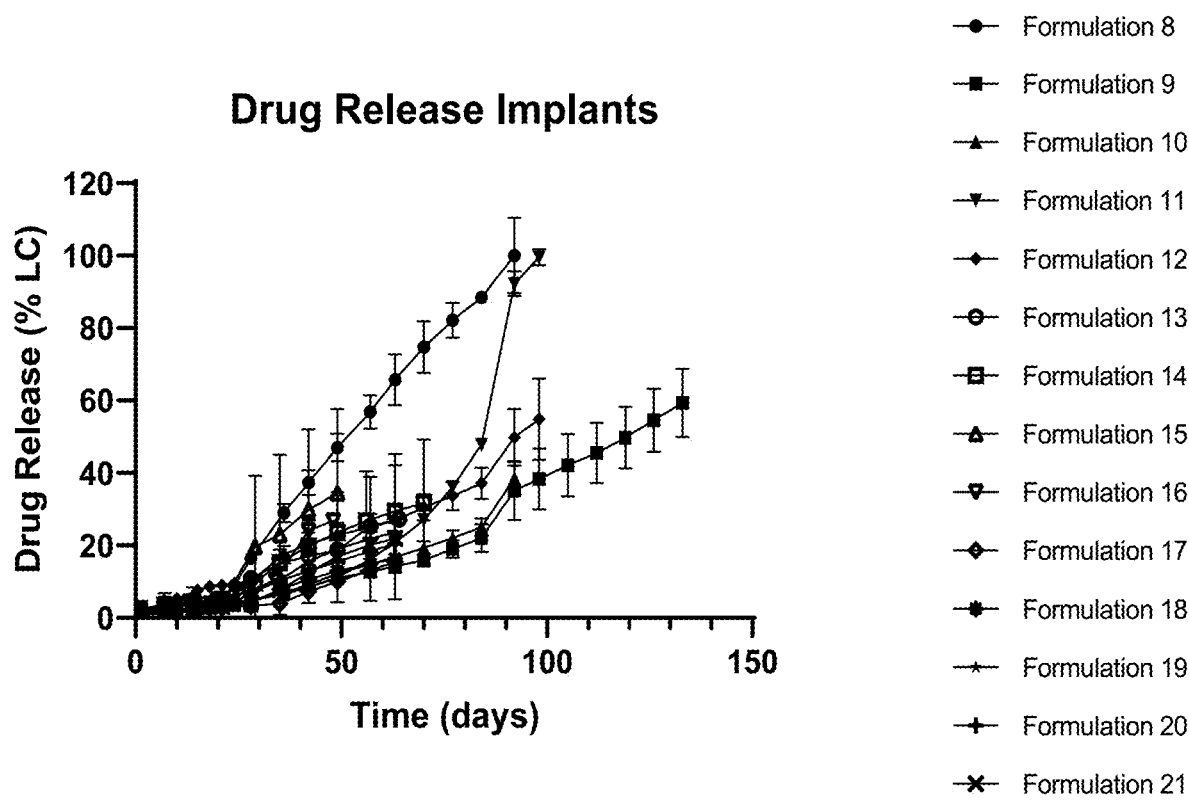
FIG. 3 depicts drug release profiles of Edonentan in implants of exemplary formulations each containing a polymer matrix incorporating Edonentan. The in vitro release results show that the combination of polymer matrix with Edonentan provides sustained release of active as determined by HPLC.
Figure 4:
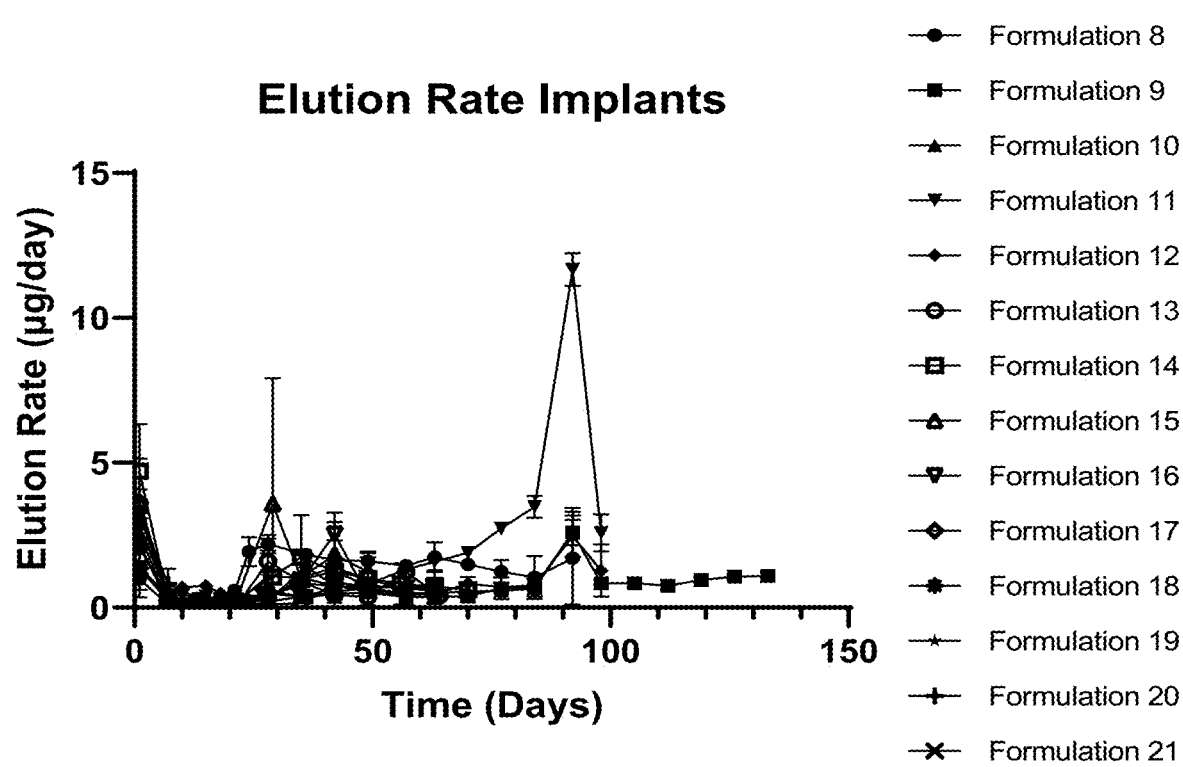
FIG. 4 depicts elution rate profiles of Edonentan in implants of exemplary formulations each containing a polymer matrix incorporating Edonentan. The in vitro release results show that the polymer matrix controls the initial release of Edonentan with the peak release ranging from day 17 to day 92, as determined by HPLC. The in vitro release results show that the amount of Edonentan released decreases with the increase of the ratio of poly-lactic acid (PLA) to poly-glycolic acid (PGA) as well as the increase of molecular weight of the polymer. The mixtures of RG753S with other faster-releasing formulations provide a long period of sustained drug release while maintaining sufficient drug release at earlier time points.

For in vitro drug release testing, three implants per each formulation were randomly cut from fiber trees and incubated in 3 mL of PBS pH 7.4 in a shaking incubator set at 37° C. and 50 rpm. The drug release profiles of the implants were sampled at designated time points and the released Edonentan content analyzed by an HPLC assay, as shown in FIG. 3. Corresponding elution rates of the Edonentan from the implants as a function of time are provided in FIG. 4. The release medium was completely replaced with fresh medium during each sampling time point.

TABLE 1

Exemplary formulations.
Edonentan Containing Sustained Delivery Formulations
(1-7) for the production of film disks

| Formulation No. | Edonentan % w/w | Polymer % w/w | | | | | | | | |
|---|---|---|---|---|---|---|---|---|---|---|
| | | RG502 | RG502H | RG503 | RG503H | RG504 | RG504H | RG753H | RG753S | 65/35 PLA/PLG |
| 1 | 30 | | | 50 | 50 | | | | | |
| 2 | 30 | | | | | | | | | 100 |
| 3 | 30 | | | | | | | 100 | | |
| 4 | 30 | 50 | 50 | | | | | | | |
| 5 | 30 | | | | | 50 | 50 | | | |
| 6 | 30 | | | 40 | 40 | | | | 20 | |
| 7 | 30 | | | 50 | 10 | | | | 40 | |

TABLE 2

Exemplary formulations.
Edonentan Containing Sustained Delivery Formulations
(8-16) for the production of implants

| Formulation No. | Edonentan % w/w | Polymer % w/w | | | | | | | | |
|---|---|---|---|---|---|---|---|---|---|---|
| | | RG502 | RG503H | RG503 | RG752S | RG753S | RG755S | RG756S | RG858S | R203S |
| 8 | 30 | | 10 | 50 | | 40 | | | | |
| 9 | 45 | 10 | | 50 | | 40 | | | | |
| 10 | 45 | 20 | | 40 | | 40 | | | | |
| 11 | 45 | 10 | | 50 | 40 | | | | | |
| 12 | 45 | 20 | | | 60 | 20 | | | | |
| 13 | 45 | 20 | 20 | 40 | | 20 | | | | |
| 14 | 45 | | 10 | 50 | | 40 | | | | |
| 15 | 45 | 10 | 10 | 30 | | 50 | | | | |
| 16 | 45 | 20 | 20 | 20 | | 40 | | | | |
| 17 | 45 | 20 | | 20 | | 60 | | | | |
| 18 | 45 | 10 | | 50 | | | 40 | | | |
| 19 | 45 | 10 | | 50 | | | | 40 | | |
| 20 | 45 | 20 | | 30 | 30 | | | | 20 | |
| 21 | 45 | 10 | | 50 | 30 | | | | 10 | |
| 22 | 45 | 20 | | 30 | 30 | | | | | 20 |

Example 3. Pharmacokinetics Study: 12-Week Ocular and Systemic Pharmacokinetic of Edonentan Intravitreal Implant in Rabbits In a nonGLP 12-week ocular and systemic pharmacokinetic study in DB rabbits, 1 Edonentan Intravitreal Implant (total implant weight 384 μg/implant; 173 μg Edonentan/implant) was administered as a single bilateral IVT injection in DB rabbits (2 animals and 4 eyes per timepoint). The implants contained 45% Edonentan in a blend of Resomer® containing 50% RG503, 10% RG502, and 40% RG752S. Rabbits were euthanized at Weeks 2, 4, 8 and 12 and drug concentrations in aqueous humor, lens, vitreous humor, retina, RPE/choroid and plasma were determined.

Ocular tissues and plasma samples were analyzed by LC-MS/MS for drug content. Reverse-phase separation was utilized using a Zorbax Eclipse Plus C18 Rapid Resolution column and mobile phases of water and acetonitrile modified with 0.1% formic acid. An Agilent 1290 UPLC coupled to an Agilent 6430 triple quadrupole mass spectrometer was used for analysis, with the mass transition of 537.21 to 439.4 Da captured for quantification. A concentration range of 1 to 200 ng/mL of Edonentan with a deuterated Edonentan internal standard at the fixed concentration of 10.6 ng/mL was used. Ocular tissues were prepared for analysis by protein precipitation and liquid-liquid extraction.

IVT sustained release delivery of 45% Edonentan in this PLGA implant demonstrated achievement of sustainable therapeutic target tissue levels of Edonentan for the duration of the study (Table 3). Results showed that implants released a cumulative total of 16%, 30%, 48%, and 100% Edonentan at 2, 4, 8, and 12 weeks, respectively.

TABLE 3

Average Edonentan concentrations in target ocular tissues and plasma at different timepoints during 12-week ocular and systemic pharmacokinetic of Edonentan intravitreal implant study in DB rabbits.

| Tissue | Edonentan Avg Concentration (ng/g) | | | |
|---|---|---|---|---|
| | Day 14 | Day 28 | Day 56 | Day 84 |
| Aqueous Humor | 0.00 | 0.00 | 1.97 | 0.00 |
| Lens | 93.33 | 131.00 | 193.06 | 489.73 |
| Vitreous Humor | 59.75 | 35.80 | 206.25 | 0.00 |
| Retina | 148.50 | 101.80 | 485.10 | 0.00 |
| RPE/Choroid | 182.99 | 126.60 | 334.90 | 107.13 |
| Plasma | BLQ | BLQ | BLQ | BLQ |
| Implant Remaining (μg) | 145 | 121 | 90 | 0 |
| % Released | 16 | 30 | 48 | 100 |

BLQ: Below limit of quantitation
LLOQ = 1 ng/mL

Example 4. Distribution Study

In vitro melanin binding of Edonentan was assessed in an in vitro assay with synthetic melanin. A concentration of 200 μM Edonentan was added into in two separate working solutions with or without melanin (1 mg/mL). A concentration of 200 μM chloroquine was used as a positive control. In this assay, Edonentan exhibited low (6.1% bound) binding to melanin. For the control, percentage of chloroquine bound to melanin (99.5%) was comparable (92-99.6% bound at pH 7.4 in 2 mg/mL melanin solution) to the literature values (Rimpela 2016).

Example 5. Toxicology Study: 2-Month Single-Dose Intravitreal Ocular Toxicity Study in Rabbits In a study of nonGLP 2-month single dose IVT ocular dose range toxicity study in DB rabbits (5 male/group), 2 or 3 Edonentan Intravitreal Implants (180 Edonentan/implant; 360 and 540 μg/eye total) or 2 Placebo Implants were administered with a 56 day evaluation period: Total implant mass was 365 μg with a diameter of approximately 300 μm and a length of 4 mm, and the implants contained 45% Edonentan in a blend of Resomer® containing 50% RG503 and 50% RG503H.

Parameters evaluated included ophthalmic examinations, ocular observations (modified Hackett and McDonald), tonometry, retinal imaging of the implant, optical coherence tomography (OCT), ERG, and toxicokinetics. Animals were euthanized on Day 56 and one eye was collected for pharmacokinetics and the other eye was collected for potential histopathology.

Ophthalmic findings included transient ocular changes (conjunctiva redness, aqueous flare, vitreous cells) in 1 of 10 eyes administered 2 or 3 Edonentan Intravitreal Implant (360 or 540 µg/eye, respectively) on Day 27. These changes fully resolved by the end of the study on Day 56. No changes in IOP, ERG, or OCT were observed.

Ocular tissues and plasma samples were analyzed by LC-MS/MS for drug content. Reverse-phase separation was utilized using a Zorbax Eclipse Plus C18 Rapid Resolution column and mobile phases of water and acetonitrile modified with 0.1% formic acid. An Agilent 1290 UPLC coupled to an Agilent 6430 triple quadrupole mass spectrometer was used for analysis, with the mass transition of 537.21 to 439.4 Da captured for quantification. A concentration range of 0.9 to 200 ng/mL of Edonentan with a deuterated Edonentan internal standard at the fixed concentration of 10.6 ng/mL was used. Ocular tissues were prepared for analysis by protein precipitation and liquid-liquid extraction.

Figure 5:
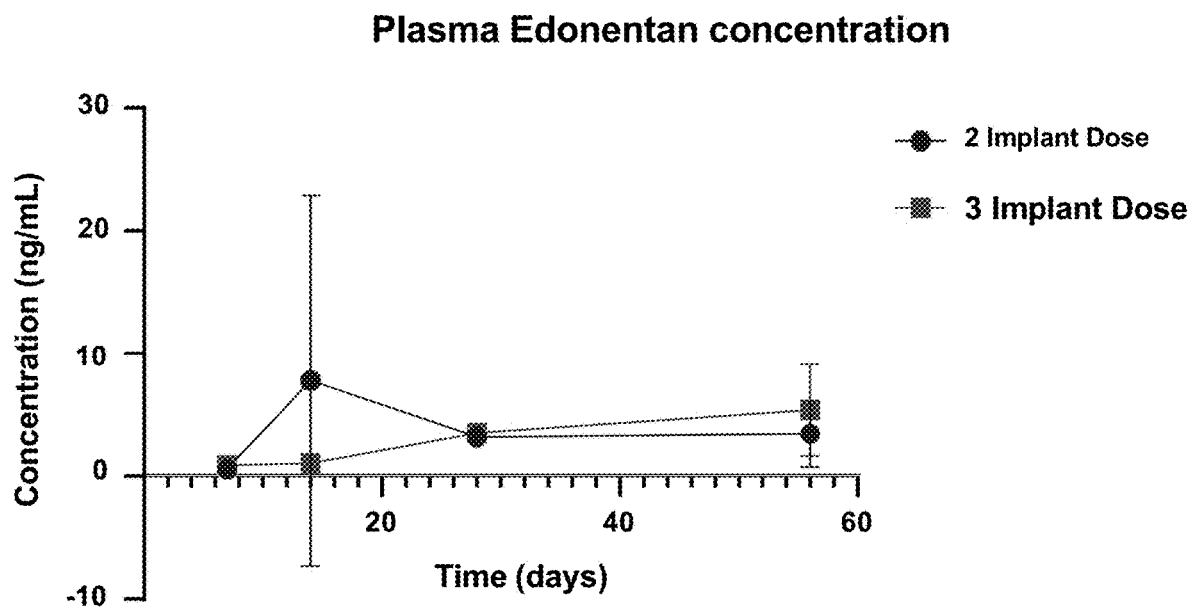
FIG. 5 depicts a time course of the Edonentan plasma levels during 8-week single-dose intravitreal ocular toxicity study in Dutch-belted rabbits in 2 and 3 implant groups.

The results showed that Edonentan level was highest in the lens at Day 56 (Table 4). The implants had almost complete release on Day 56 with detectable plasma levels of 3.4 ng/mL and 5.4 ng/mL for 2 and 3 Edonentan Intravitreal Implants, respectively. The plasma levels over time are presented in FIG. 5.

TABLE 4

Levels of Edonentan at various ocular tissues and plasma at day 57 post ivt administration.

| Tissue (concentration) | 2 Edonentan Intravitreal Implants | 3 Edonentan Intravitreal Implants |
|---|---|---|
| Aqueous Humor (ng/mL) | 3.1 | 49.8 |
| Cornea (ng/g) | 0.0 | 1.8 |
| ICB (ng/g) | 0.1 | 28.8 |
| Lens (ng/g) | 787.0 | 1045.6 |
| Vitreous Humor/Implant (ng/g) | 21.1 | 26.5 |
| Retina (ng/g) | 0.0 | 7.2 |
| RPE/Choroid (ng/g) | 0.0 | 0.0 |
| Optic Nerve Head (ng/g) | 0.2 | 14.1 |
| Plasma (ng/mL) | 3.4 | 5.4 |

Eyes collected for histological examination were processed (n=2 animals per group). Other than a few vitreal cells and incidental retinal folds, which are likely sectioning artifacts, no histologic abnormalities were noted in any of the eyes of the groups. Based on the examination of these eyes on histology, the placebo implants and implants containing 360 µg or 540 µg of Edonentan appeared to be well-tolerated.

Example 6. Toxicology Study: 3-Month Single-Dose Intravitreal Ocular Toxicity Study in Rabbits In the GLP 3-month single dose IVT ocular toxicity study with 1-month recovery in DBrabbits, a formulation of Edonentan Intravitreal Implants (total implant mass 440 µs; 200 µg Edonentan with a diameter of 340 µm and a length of 4 mm) is evaluated. The implant contains 45% Edonentan in a blend of Resomer® containing 50% RG503, 10% RG502, and 40% RG753S.

Group 1 is given 3 Placebo Implants in the left eye (0 µg/eye) and 2 Placebo Implants in the right eye (0 µg/eye) with sham injection in the right eye. Group 2 is given 2 Edonentan Intravitreal Implants in the left eye (400 µg/eye) and the right eye is untreated. Group 3 is given 3 Edonentan Intravitreal Implants in the left eye (600 µg/eye) with sham injection in the right eye. The study design is presented below in Table 5.

TABLE 5

Study design of 3-month single-dose intravitreal ocular toxicology study in rabbits.

| Group | OD | OS Edonentan Intravitreal Implant Dose (µg) | Main Phase Month 3 M/F | Recovery Phase Month 4 M/F |
|---|---|---|---|---|
| 1 | 2 Placebo Implants (0 µg) | 3 Placebo Implants (0 µg) | 4/4 | 2/2 |
| 2 | Untreated Control | 2 Edonentan Intravitreal Implants (400 µg) | 4/4 | 2/2 |
| 3 | Sham Injection | 3 Edonentan Intravitreal Implants (600 µg) | 4/4 | 2/2 |

OD = right eye;
OS = left eye

A 12-week main phase evaluation (4 rabbits/sex/group) was selected based on the observation of Edonentan detectable drug concentrations present in target (RPE/choroid) and nontarget (lens) tissue at 12 weeks based on ocular pharmacokinetic study in rabbits. A 1-month recovery phase is selected based on anticipated lower or absent tissue concentrations at the 4-month timepoint.

The high dose of 3 Edonentan Intravitreal Implants represents a 1.5× ocular safety margin with respect to implant number compared to the highest planned clinical dose of 2 Edonentan Intravitreal Implants. The high dose of 3 Edonentan Intravitreal Implants (600 µg/eye) also represents a 5× ocular dose safety margin compared to the highest planned clinical dose of 2 Edonentan Implants (400 µg/eye) based on species differences in vitreal volume of 1.4 mL in rabbits (Struble 2014) and 4.6 mL in humans (Caruso 2020, Azhdam 2020). Parameters and frequency of evaluation for this study are listed in Table 6.

TABLE 6

Parameters of 3-month intravitreal ocular toxicity study in rabbits.

| Parameter | Frequency |
|---|---|
| Viability/Health Monitoring | Twice daily |
| Clinical Examinations (Cage-side Observations) | Pretest and daily |

TABLE 6-continued

Parameters of 3-month intravitreal ocular toxicity study in rabbits.

| Parameter | Frequency |
|---|---|
| Detailed clinical observations | Pretest and weekly |
| Body Weight | Pretest and weekly |
| Food evaluation | Weekly qualitative |
| Ophthalmic Examination (slit lamp biomicroscopy, indirect ophthalmoscopy) | Pretest and Days 3, 8, 15, 29, 57, 84, 112 |
| Intraocular Pressure Measurements | Concurrent with ophthalmic examinations |
| Wide Angle Fundus Imaging/Fundus Photography | Concurrent with ophthalmic examinations |
| Electroretinography | Pretest and prior to necropsy |
| Clinical Pathology (hematology, coagulation, clinical chemistry) | Pretest and prior to necropsy |
| Toxicokinetic Blood Collection for Toxicokinetic Analysis | Group 1: Day 2<br>Group 2 and 3: Days 2, 29, 57, 84, 112 |
| Necropsy (Full) | Terminal Necropsy: Month 3 Recovery Necropsy: Month 4 |
| Organ weights | Standard list |
| Tissue Collection | Full, including eyes, attached optic nerve and extraocular tissues (upper and lower eyelids, lacrimal glands, Harderian glands, nictitating membrane, gross lesions. |
| Ocular Histology/Histopathology | All Groups: Eye with attached optic nerve, eyelids, lacrimal glands, nictitating membranes, gross lesions<br>Group 1 and 3: Full tissue list<br>Group 2: Systemic target organs |
| Pathology Peer Review | Yes |

Ocular histopathology will include assessment of a full range of ocular tissues. At least 3 sagittal sections of each eye will be prepared, including full assessment of cone dense retina (visual streak) in one or several sections. Consideration of in-life toxicity regarding sectioning and assessment of eye will be included. The study pathologist will confirm that the cone dense visual streak was adequately assessed.

Example 7. Toxicology Study: 6-Month Single Dose Intravitreal Ocular Toxicology Study in Monkeys The Edonentan Intravitreal Implant formulation and dose selection of the GLP 6-month single dose IVT ocular toxicity study in cynomolgus monkeys is similar to that described above for the GLP 3-month IVT ocular toxicity study in rabbits. The high dose of 3 Edonentan Implants represents a 1.5× ocular safety margin in implant number compared to the highest planned clinical dose of 2 Edonentan Implants. The high dose of 3 Edonentan Implants (600 µg/eye) also represents a 3.5× ocular dose safety margin compared to the highest planned clinical dose of 2 Edonentan Implants (400 µg/eye) based on species differences in vitreal volume between monkeys (2.0 mL) and humans (4.6 mL) (Caruso 2020, Azhdam 2020). Details of the study is shown in Table 7. Parameters and frequency of evaluation for this study is listed in Table 8.

TABLE 7

Study design of 6-month single-dose GLP ocular toxicology study in monkeys.

| Group | OD | OS Edonentan Intravitreal Implant Dose (µg) | Main Phase Month 6 M/F | Recovery Phase Month 7 M/F |
|---|---|---|---|---|
| 1 | 2 Placebo Implants (0 µg) | 3 Placebo Implants (0 µg) | 4/4 | 2/2 |
| 2 | Untreated Control | 2 Edonentan Intravitreal Implants (400 µg) | 4/4 | 2/2 |
| 3 | Sham Injection | 3 Edonentan Intravitreal Implants (600 µg) | 4/4 | 2/2 |

TABLE 8

Parameters and frequency of evaluation of 6-month ocular toxicity study in monkeys.

| Parameter | Frequency |
|---|---|
| Viability/Health Monitoring | Twice daily |
| Clinical Examinations (Cage-side Observations) | Pretest and daily |
| Detailed clinical observations | Pretest and weekly |
| Body Weight | Pretest and weekly |
| Food evaluation | Weekly qualitative |
| Ophthalmic Examination (slit lamp biomicroscopy, indirect ophthalmoscopy) | Pretest and Days 3, 8, 15, and monthly prior to necropsy |

TABLE 8-continued

Parameters and frequency of evaluation of 6-month ocular toxicity study in monkeys.

| Parameter | Frequency |
|---|---|
| Intraocular Pressure Measurements | Concurrent with ophthalmic examinations |
| Wide Angle Fundus Imaging/Fundus Photography | Concurrent with ophthalmic examinations |
| Electroretinography | Pretest and prior to necropsy |
| Clinical Pathology (hematology, coagulation, clinical chemistry, urinalysis) | Pretest and prior to necropsy |
| Safety pharmacology parameters of cardiovascular and respiratory function. | Pretest, Week 3 and during Months 3, 6 (prior to Month 6 necropsy) and 7. |
| Toxicokinetic Blood Collection for Toxicokinetic Analysis | Group 1: Day 2<br>Group 2 and 3: Days 2, 29, 57, 85, 113, 141, 169 |
| Necropsy (Full) | Terminal Necropsy: Month 6 Recovery Necropsy: Month 7 |
| Organ weights | Standard list |
| Tissue Collection | Full, including eyes, attached optic nerve and extraocular tissues (upper and lower eyelids, lacrimal glands, Harderian glands, nictitating membrane, gross lesions) |
| Ocular Histology/Histopathology | All Groups: Eye with attached optic nerve, eyelids, lacrimal glands, nictitating membranes, gross lesions<br>Group 1 and 3: Full tissue list<br>Group 2: Systemic target organs |
| Pathology Peer Review | Yes |

Ocular histopathology includes assessment of a full range of ocular tissues. At least 3 horizontal (transverse) sections of each eye are prepared, including full assessment of cone dense retina (macula) in one or several sections. Consideration of in-life toxicity with regard to sectioning and assessment of eye is included. The study pathologist confirms that the cone dense macula was adequately assessed.

Example 8. Toxicology Study: GLP 1-Month Oral Toxicity Study in Rats

To evaluate systemic toxicity of Edonentan, a GLP 1-month oral toxicity study in rats is conducted. This 1-month oral toxicity study in Sprague-Dawley rats consists of a 1-month main phase and a 2-week recovery phase. The highest dose selected in this study is 5 mg/kg/day and lower doses of 1.5 and 0.5 mg/kg/day are selected to evaluate dose-response relationships. The high dose selection of 5 mg/kg/day for this study is in line with the 0.83 mg/kg human dose previously tested, estimates for high dose selection based on comparisons between BMS-193884 and BMS-207940 literature data, as well as ICH M3(R2) guidelines for high dose selection. Study design is listed below in Table 9. Parameters and frequency of evaluation is listed below in Table 10. Safety pharmacology evaluation of central nervous system function is based on oral $T_{max}$ of 0.4 hour (Murugesan 2003).

TABLE 9

Study Design of GLP 1-Month Oral Toxicity Study in Rats

| Group | Dose Volume (mL/kg) | Dose Conc (mg/mL) | Dose (mg/kg/day) | Animal Number | | |
|---|---|---|---|---|---|---|
| 1 | 10 | 0 | 0 | Main Day 29 | Recovery Day 43 | TK Satellite |
| 2 | 10 | 0.05 | 0.5 | | | |
| 3 | 10 | 0.15 | 1.5 | | | |
| 4 | 10 | 0.5 | 5.0 | | | |

TABLE 10

Parameters and frequency of evaluation of GLP 1-month oral toxicity study in rats

| Parameter | Frequency |
|---|---|
| Viability | Twice daily |
| Clinical observations | Pretest and daily |
| Body Weight | Pretest and weekly |
| Food evaluation | Pretest and weekly |

Example 9. Genotoxicity Study

An in vitro genotoxicity battery (Ames and in vitro micronucleus assay in human thymidine kinase heterozygote (TK6) cells) and an in vivo oral micronucleus study in rats is conducted.

Example 10. A Study of the Safety, Tolerability, Pharmacodynamics and Pharmacokinetics of Edonentan Intravitreal Implant A study of the safety, tolerability, pharmacodynamics and pharmacokinetics of Edonentan Intravitreal Implant in patients with diabetic retinopathy and patients with glaucoma is described in Table 11.

TABLE 11

Study of Edonentan Intravitreal Implant

| | |
|---|---|
| Study Population | Patients with diabetic retinopathy without active center-involving and/or clinically significant diabetic macular edema (DME) and patients with glaucoma |
| Sample Size | Up to approximately 57 patients |
| Study Duration | 6 months treatment period plus 1 month extended safety follow-up |
| Study Objectives | To investigate the safety, tolerability, pharmacodynamics and pharmacokinetics of Edonentan Intravitreal Implant in patients with diabetic retinopathy and patients with glaucoma |
| Study Design | Single ascending dose (SAD)/proof of activity design. The first study is an open-label and single ascending dose design. Patients receive a single administration of one of two dose strengths of Edonentan Intravitreal Implant (200 μg and 400 μg). The second study is an open-label and proof of activity design and the study evaluates maximum tolerated dose determined from the first study. |
| Inclusion Criteria | Subjects meet the following criteria:<br>1. Able to provide informed consent<br>2. 18 or older<br>3. Diagnosis of DR secondary to diabetes mellitus Type 1 or 2<br>4. Study 1: patients with poor vision due to severe ischemia and/orvision threatening complications;<br>5. Study 2: a) DR cohort: DR severe NPDR to mild to moderate PDR(DRSS ranging from 53 to 65) and/or b) glaucoma cohort: stable, advanced primary open angle glaucoma |
| Exclusion Criteria | Subjects do not have any of the following:<br>1. History of hypersensitivity to any of the study drugs or to drugs of similar chemical classes<br>2. Presence of any active center-involving and/or clinically significant DME<br>3. Active or history of retinal detachment in the study eye<br>4. Female who are pregnant, nursing, or planning a pregnancy or whoare of childbearing potential not willing to remain abstinent or use contraception during the study<br>5. Male who are not willing to remain abstinent or use a condom |
| Study Assessments | Safety and tolerability are assessed by:<br>1. Adverse events<br>2. Vital signs<br>3. Safety laboratory evaluations |

Example 11. Pharmacokinetics Study: 12-Week Ocular and Systemic Pharmacokinetic of Edonentan Intravitreal Implants in Rabbits In a nonGLP 12-week ocular and systemic pharmacokinetic study in DB rabbits, 2 Edonentan Intravitreal Implants from either the injection molding (IM) or ram extrusion (RE) manufacturing process (total implant weight IM 423 μg/implant; 380 μg Edonentan/2 implants, RE 461 μg/implant, 415 μg Edonentan/2 implants) were administered as a single bilateral IVT injection in DB rabbits (2 animals and 4 eyes per timepoint). The implants contained 45% Edonentan in a blend of Resomer® containing 50% RG503, 10% RG502, and 40% RG753S. Rabbits were euthanized at Weeks 4, 8, 10, 11 and 12 and drug concentrations in aqueous humor, lens, vitreous humor, retina, RPE/choroid and plasma were determined.

Ocular tissue and plasma were analyzed for Edonentan content using an analytical method based on protein precipitation and liquid-liquid extraction followed by reverse-phase LC-MS/MS analysis. An Agilent 1290 UPLC coupled to an Agilent 6430 triple quadrupole mass spectrometer was used for analysis. The quantitation range for Edonentan was 1 to 250 ng/mL. Tissue and plasma samples were homogenized and extracted with 0.1% formic acid in acetonitrile which was spiked with deuterated Edonentan at approximately 10 ng/mL. The extracts were analyzed using reversed-phase liquid chromatographic separation with tandem mass spectrometric detection in the positive ion mode following the quantitative transition m/z 537.2 to 439.1 for Edonentan and m/z 540.2 to 442.1 for deuterated Edonentan.

Figure 6:
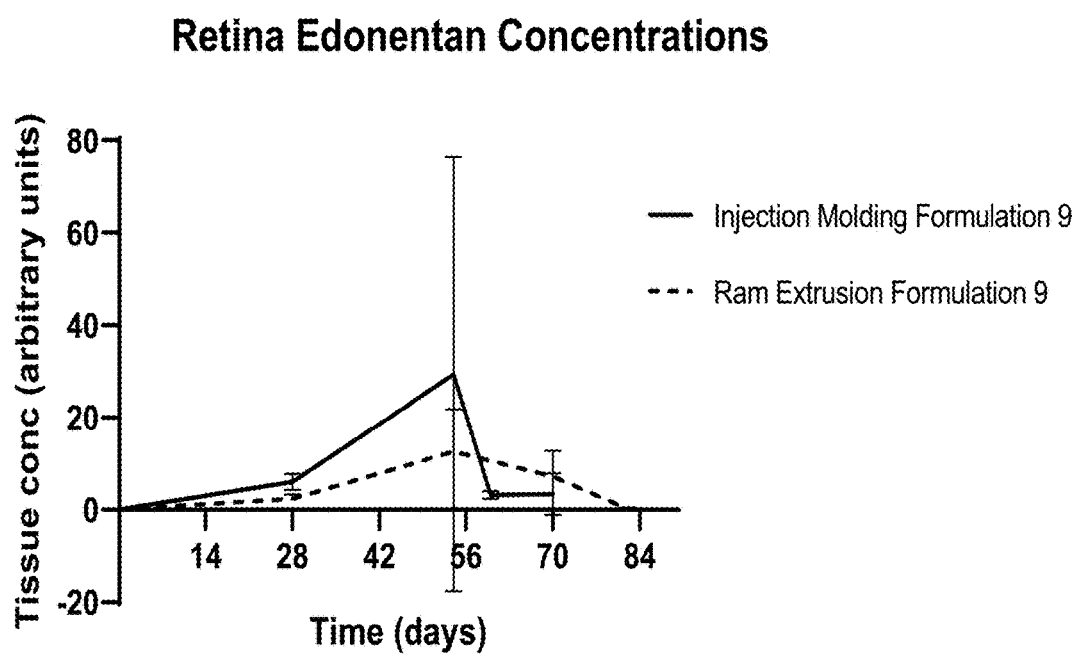
FIG. 6 depicts a time course of Edonentan retina levels during 12-week single dose intravitreal ocular pharmacokinetic study in Dutch-belted rabbits dosed with 2 implants of injection molded and ram extruded product.
Figure 7:
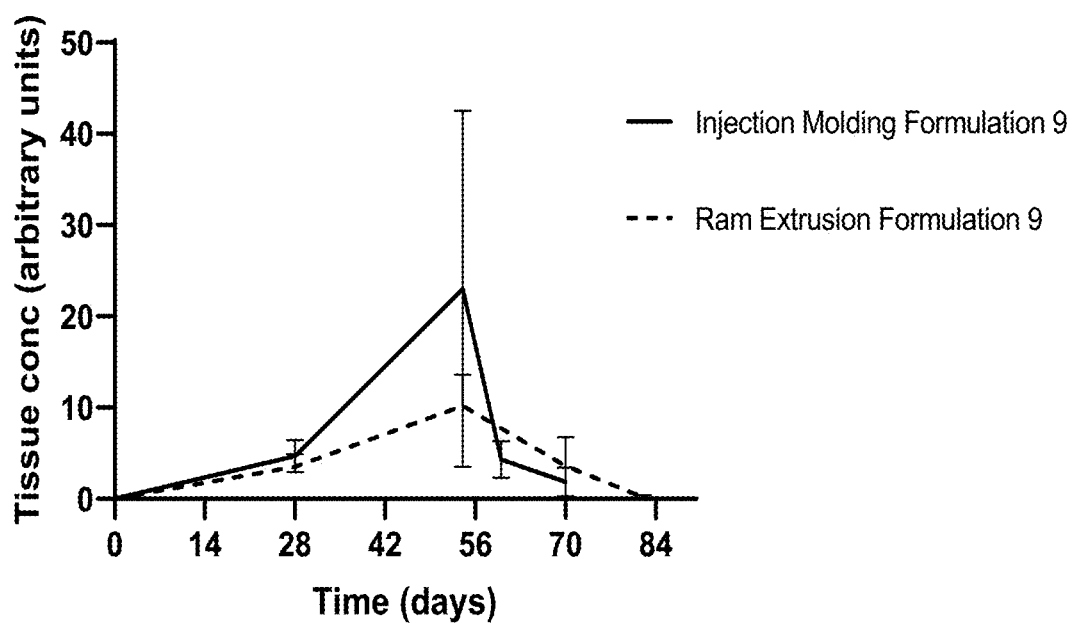
FIG. 7 depicts a time course of Edonentan RPE/choroid levels during 12-week single dose intravitreal ocular pharmacokinetic study in Dutch-belted rabbits dosed with 2 implants of injection molded and ram extruded product.
Figure 8:
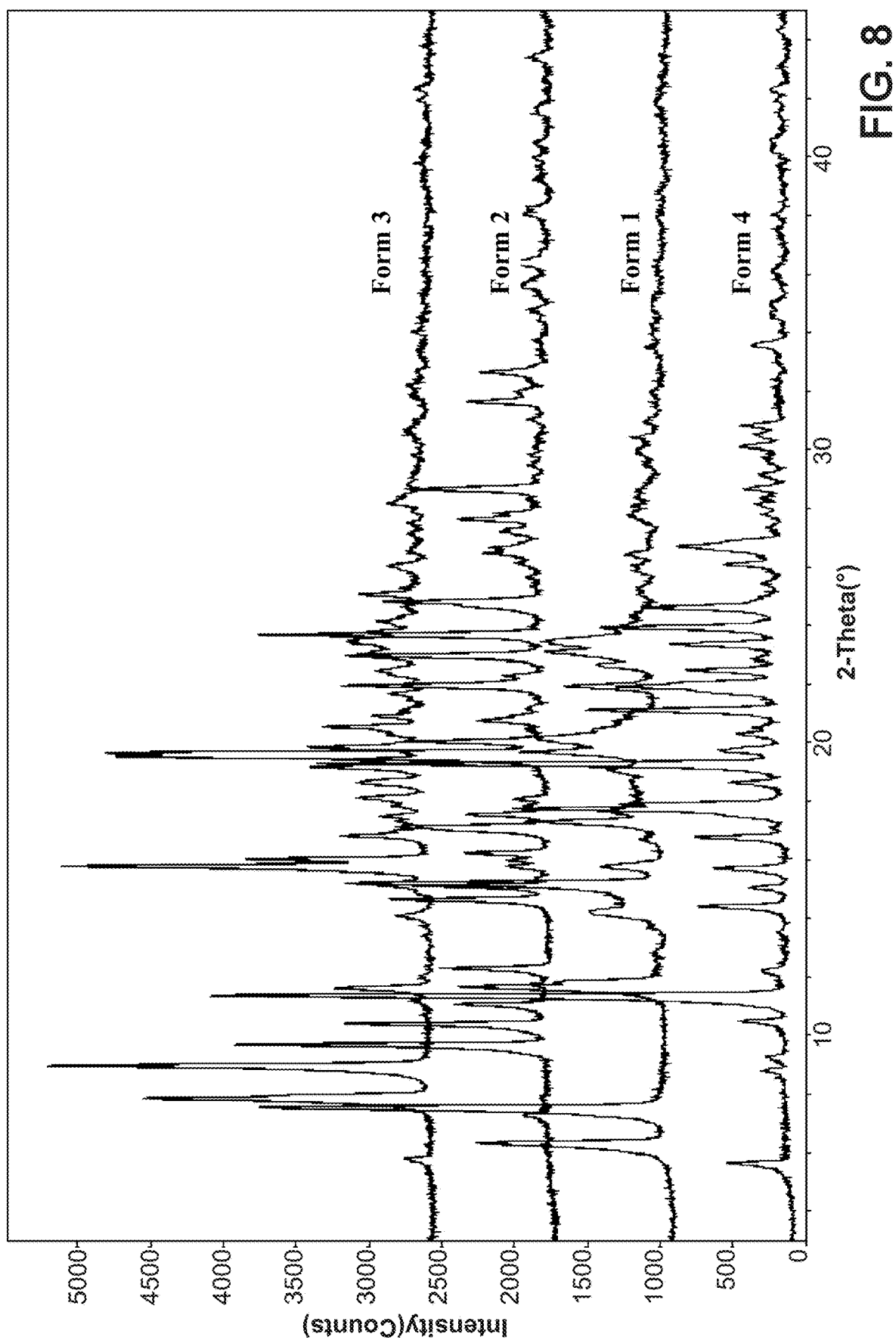
FIG. 8 depicts an exemplary overlay of XRPD pattern of Forms 1-4.

IVT sustained release delivery of 45% Edonentan in this PLGA implant demonstrated achievement of sustainable therapeutic target tissue levels of Edonentan for the duration of the study (FIG. 6, FIG. 7). The cumulative total of Edonentan released from implants was 100% at 8 weeks (Table 12).

TABLE 12

Cumulative Edonentan released from implants during 12 week ocular and systemic pharmacokinetic of Edonentan intravitreal implant in rabbit study.

| | % Released | |
|---|---|---|
| Timepoint | Injection Molded Edonentan Implants | Ram Extruded Edonentan Implants |
| Day 28 | 30.3 | 27.7 |
| Day 54 | 83.9 | 68.7 |
| Day 60 | 96.1 | NT |
| Day 70 | 96.0 | 94.5 |
| Day 82 | NT | 99.9 |

NT: not tested

Example 15. Crystalline Forms of Edonentan

Exemplary Method of Preparing Crystalline Form 1

Figure 9:
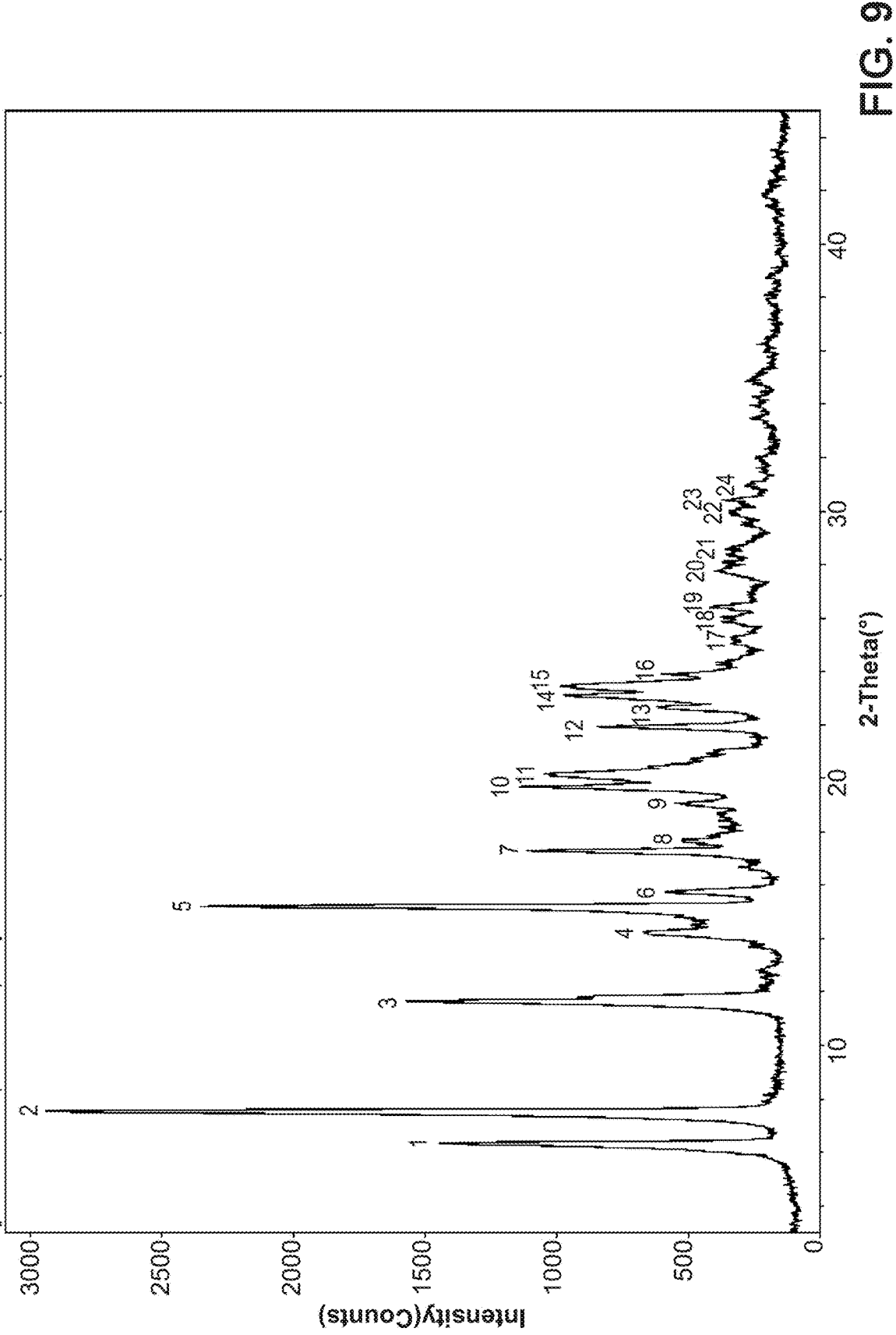
FIG. 9 depicts an exemplary XRPD pattern of Form 1.
Figure 13:
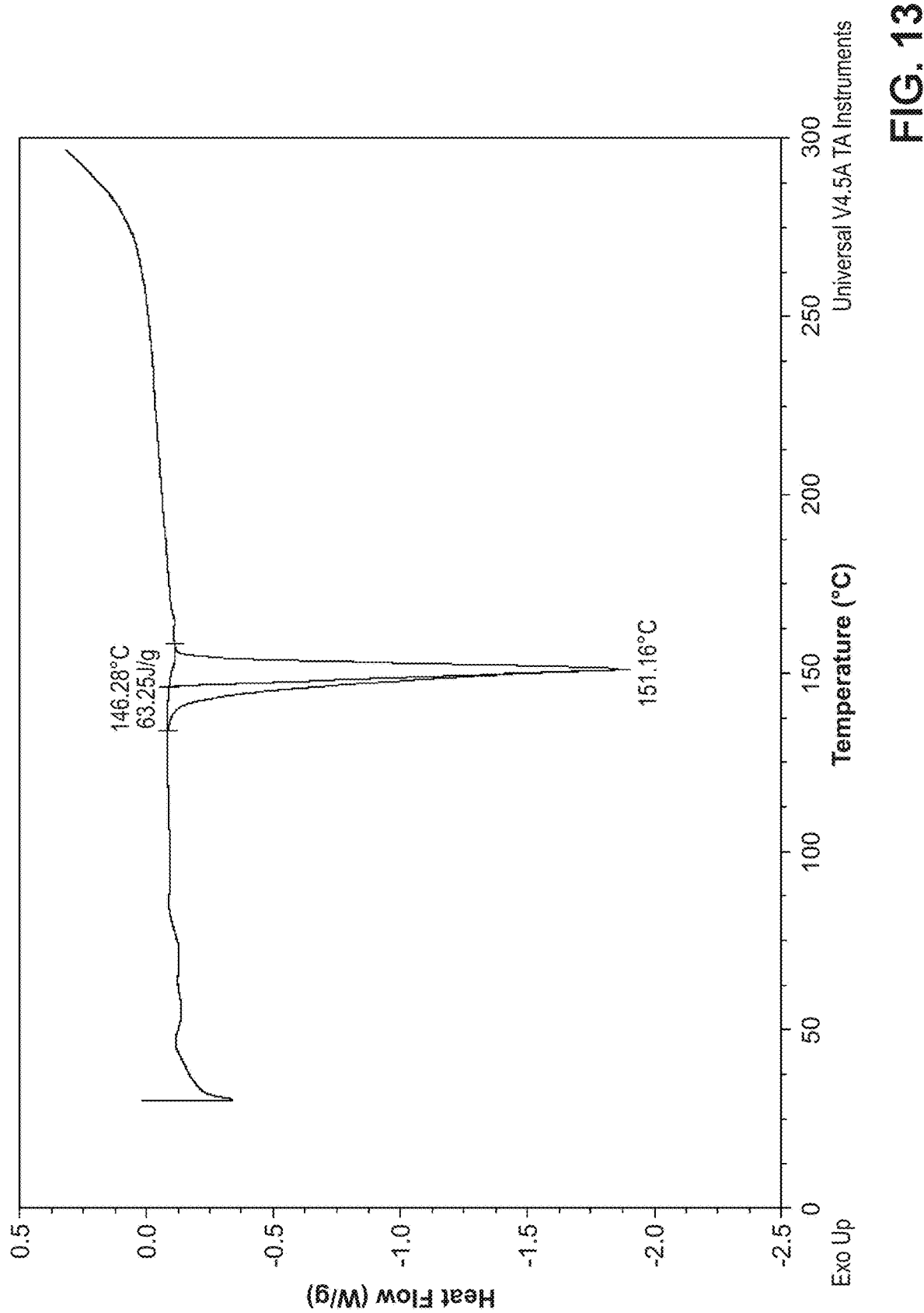
FIG. 13 depicts an exemplary DSC curve of Form 1.

Amorphous Edonentan (840 mg) was dissolved in 12 mL of IPA. The resulting solution was filtered and the filter was washed with additional 2.5 mL of IPA. The filtrated was concentrated to dryness, dissolved in 11.8 mL of IPA and heated with stirring to 60° C. Then, 18 mL of warm water was added dropwise at 60° C. while stirring vigorously and the solution was stirred at 60° C. for 1 h. The solution was slowly cooled to 25° C., filtered and dried under vacuum at 25° C. to provide 660 mg of crystalline Form 1 (XRPD and DSC in FIG. 9 and FIG. 13, respectively).

Exemplary Method of Preparing Crystalline Form 2

Figure 10:
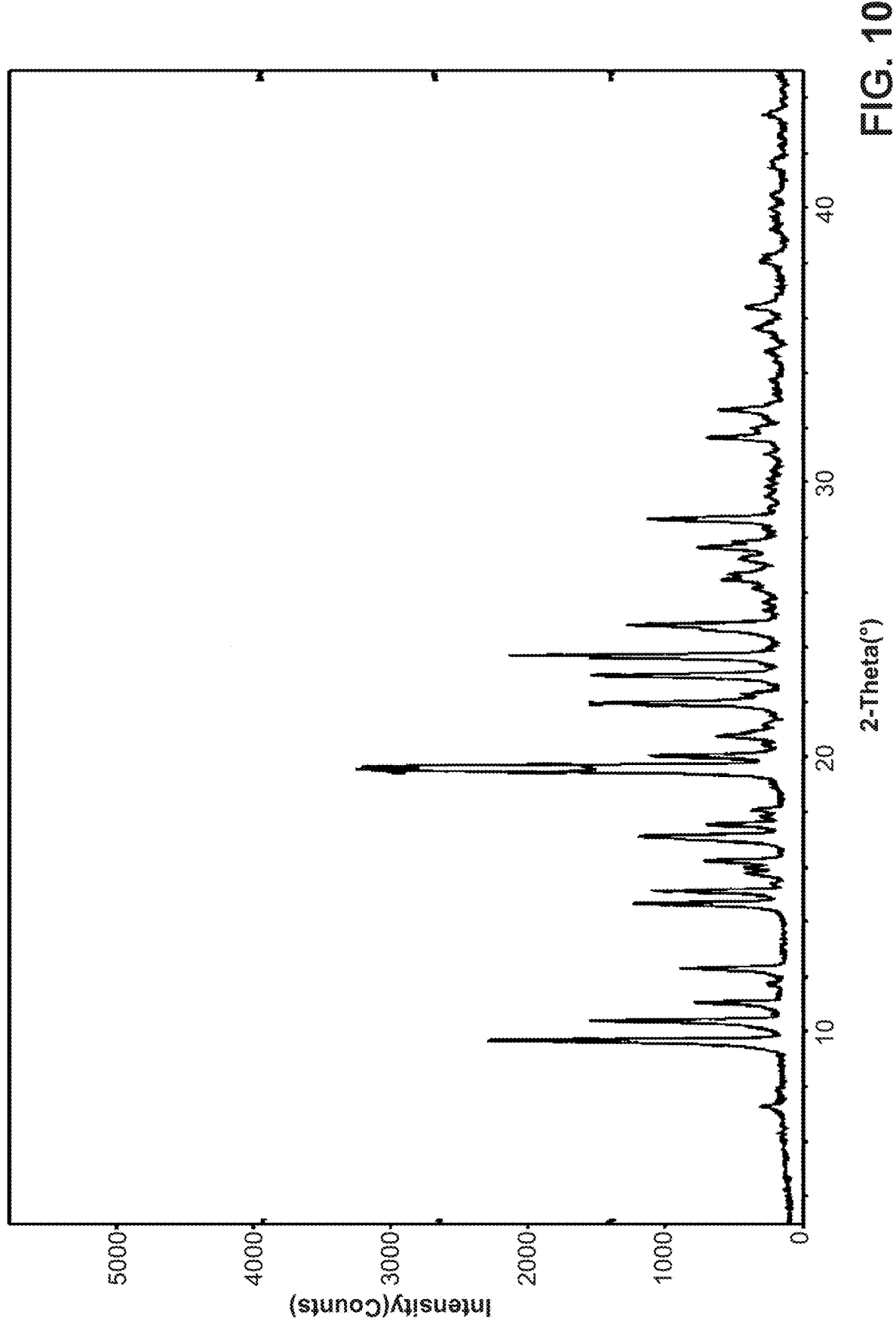
FIG. 10 depicts an exemplary XRPD pattern of Form 2.
Figure 14:
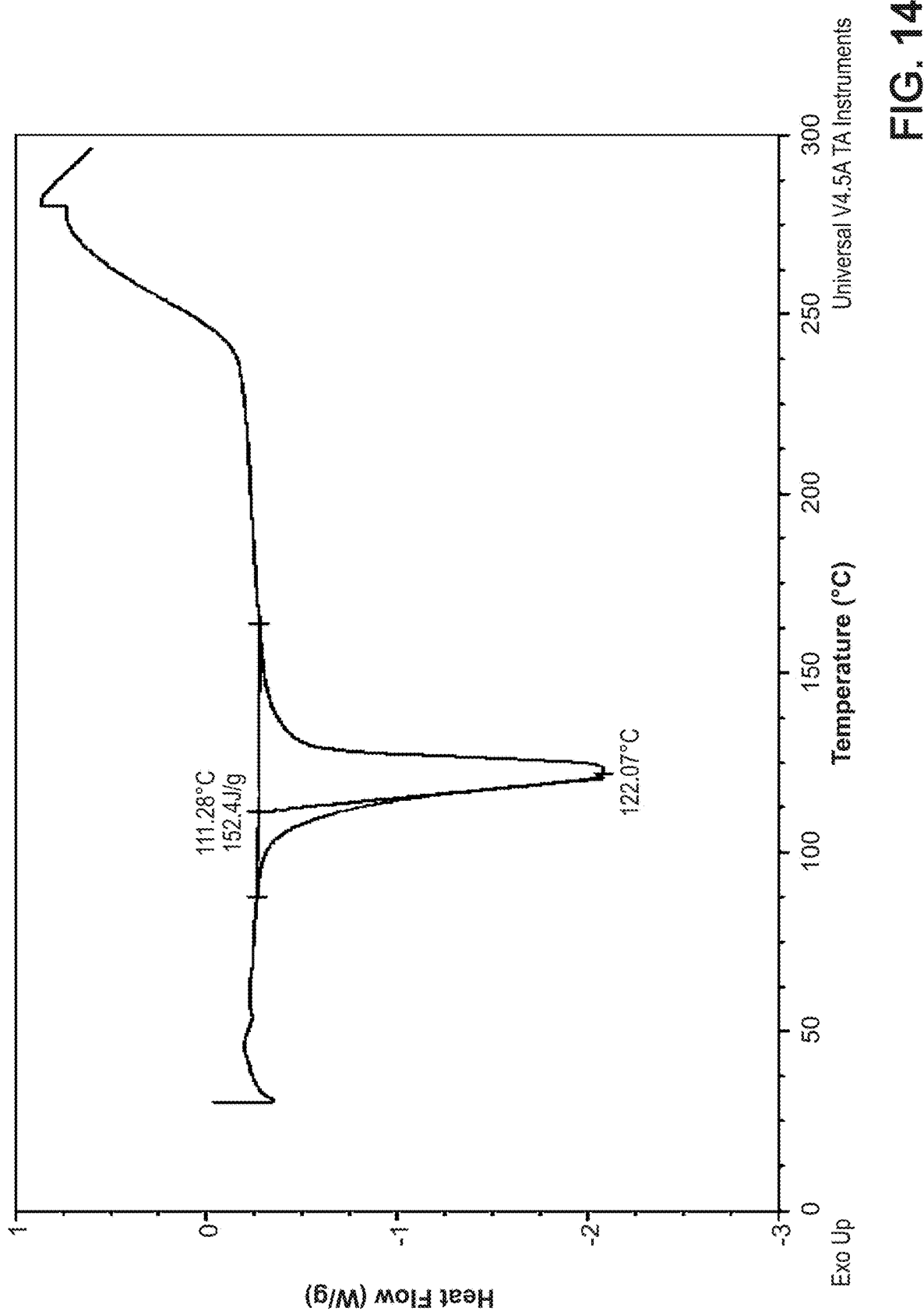
FIG. 14 depicts an exemplary DSC curve of Form 2.

Amorphous Edonentan (250 mg) was dissolved in 3.5 mL of IPA. The resulting solution was filtered and the filter was washed with additional 0.25 mL of IPA. The solution was then heated to 60° C. whereupon 7.5 mL of warm water was added dropwise at 60° C. while stirring vigorously and then stirred at 60° C. for 1 h. After slowly cooling to 25° C., the mixture was filtered to provide crystalline Form 2 (XRPD and DSC in FIG. 3 and FIG. 7, respectively). Alternatively, a preferred method of preparing crystalline Form 2 is as follows. Amorphous Edonentan (1 g) was slurried in 20 mL of water at 25° C. for 15 hours. The solution was then filtered to give the crystalline Form 2 (XRPD and DSC in FIG. 10 and FIG. 14, respectively).

Exemplary Method of Preparing Crystalline Form 3

Figure 11:
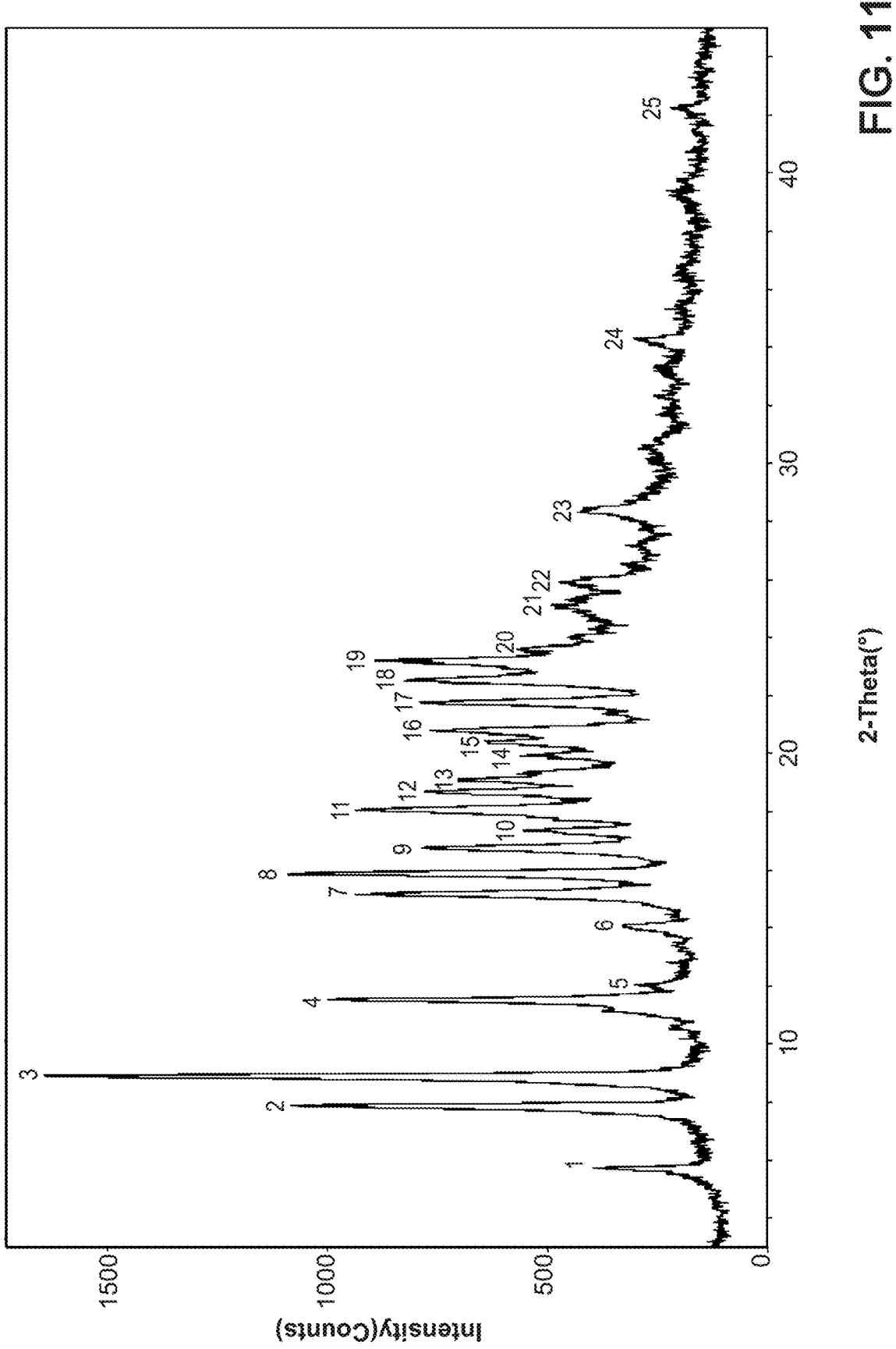
FIG. 11 depicts an exemplary XRPD pattern of Form 3.
Figure 12:
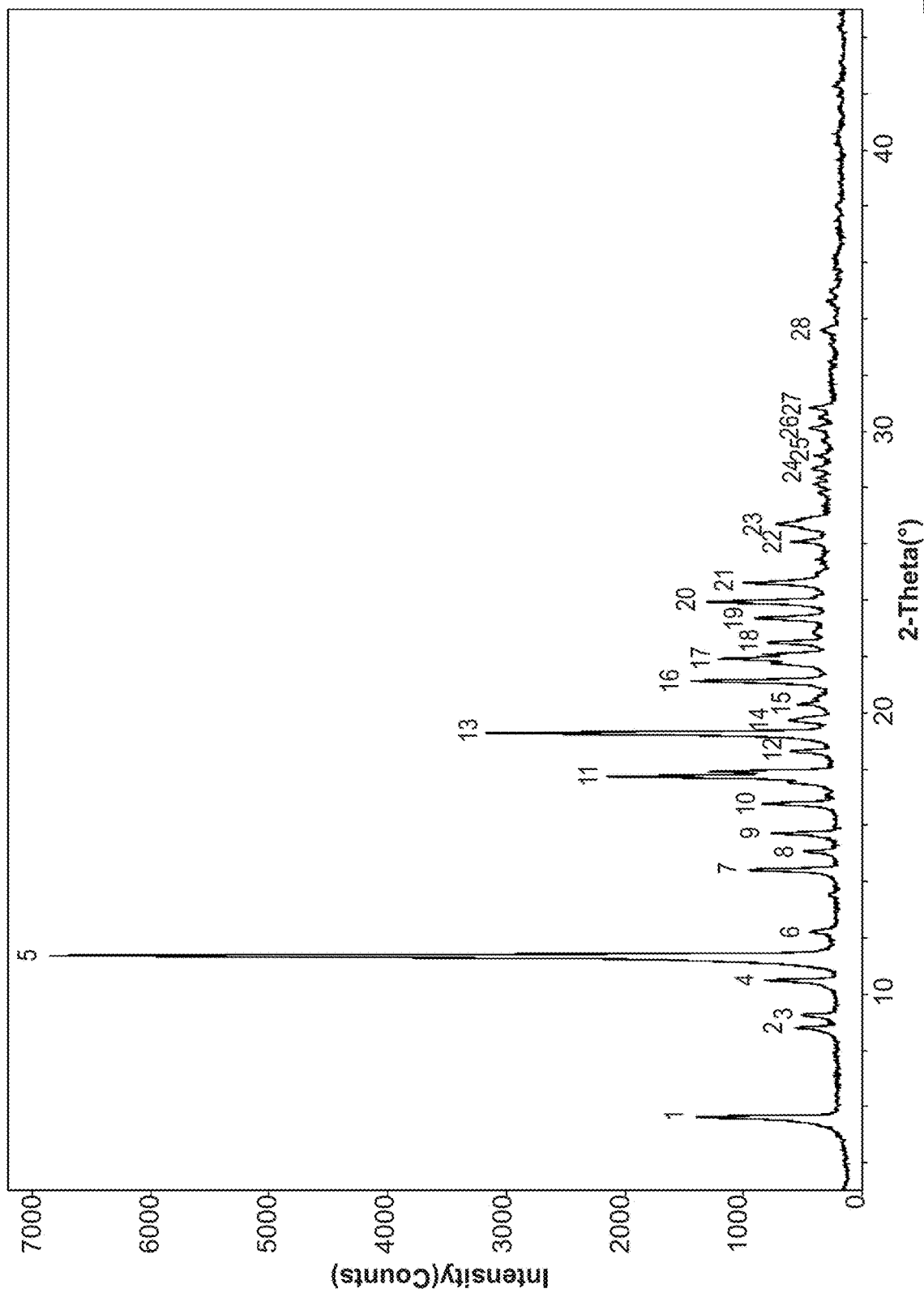
FIG. 12 depicts an exemplary XRPD pattern of Form 4.
Figure 15:
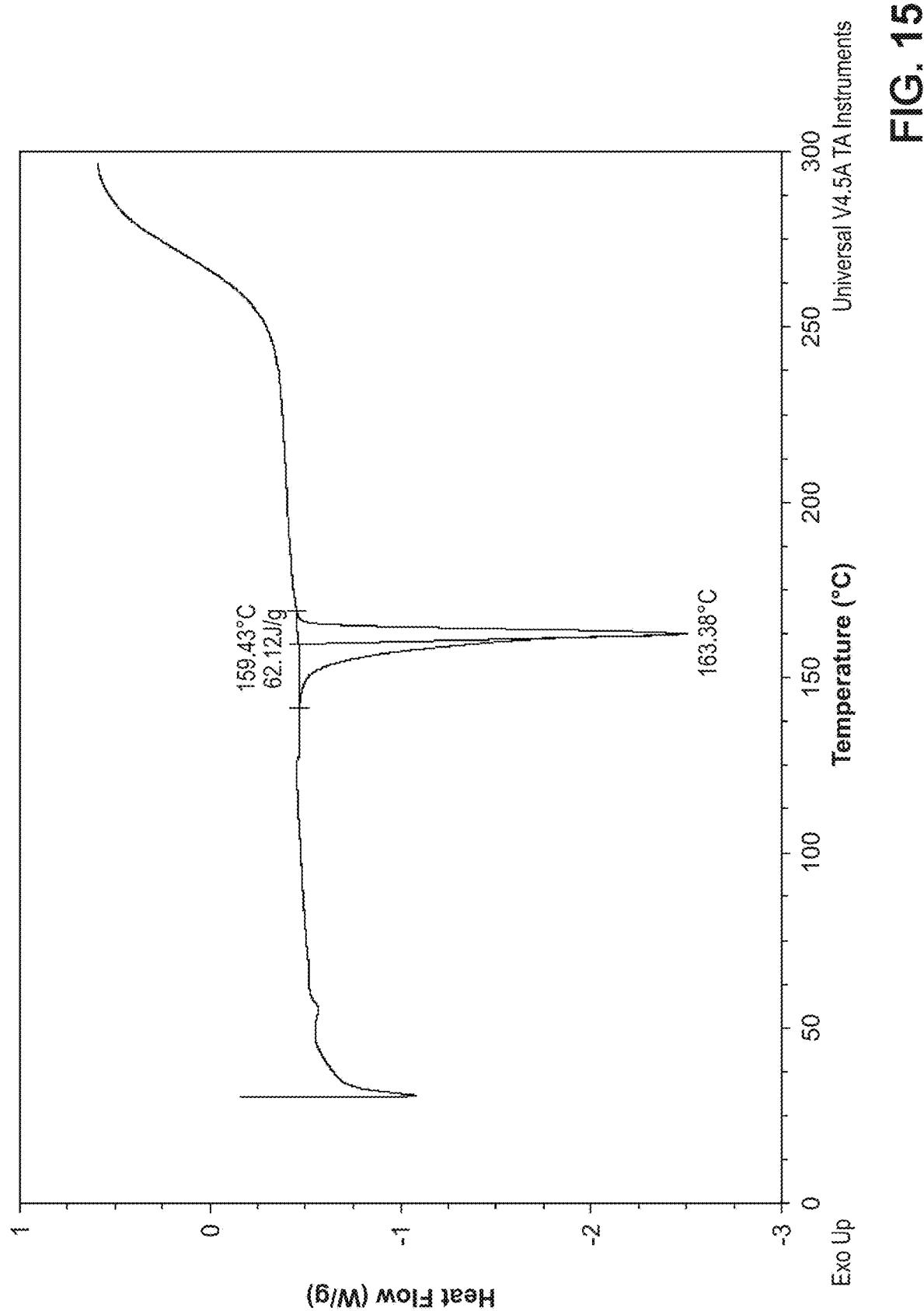
FIG. 15 depicts an exemplary DSC curve of Form 3.

Amorphous Edonentan (250 mg) was dissolved in 0.5 mL of ethyl acetate. The resulting solution was filtered and heated to 60° C., and 1.5 mL of hexane was added dropwise at 60° C. while stirring vigorously. To the resulting slightly cloudy solution, 0.1 mL of ethyl acetate was added, resulting in a clear solution which was then stirred at 60° C. for 1 h. The solution was slowly cooled to 25° C. and the resulting precipitate was filtered to provide crystalline Form 3 (XRPD and DSC in FIG. 11 and FIG. 15, respectively).

Exemplary Method of Preparing Crystalline Form 4

Figure 16:
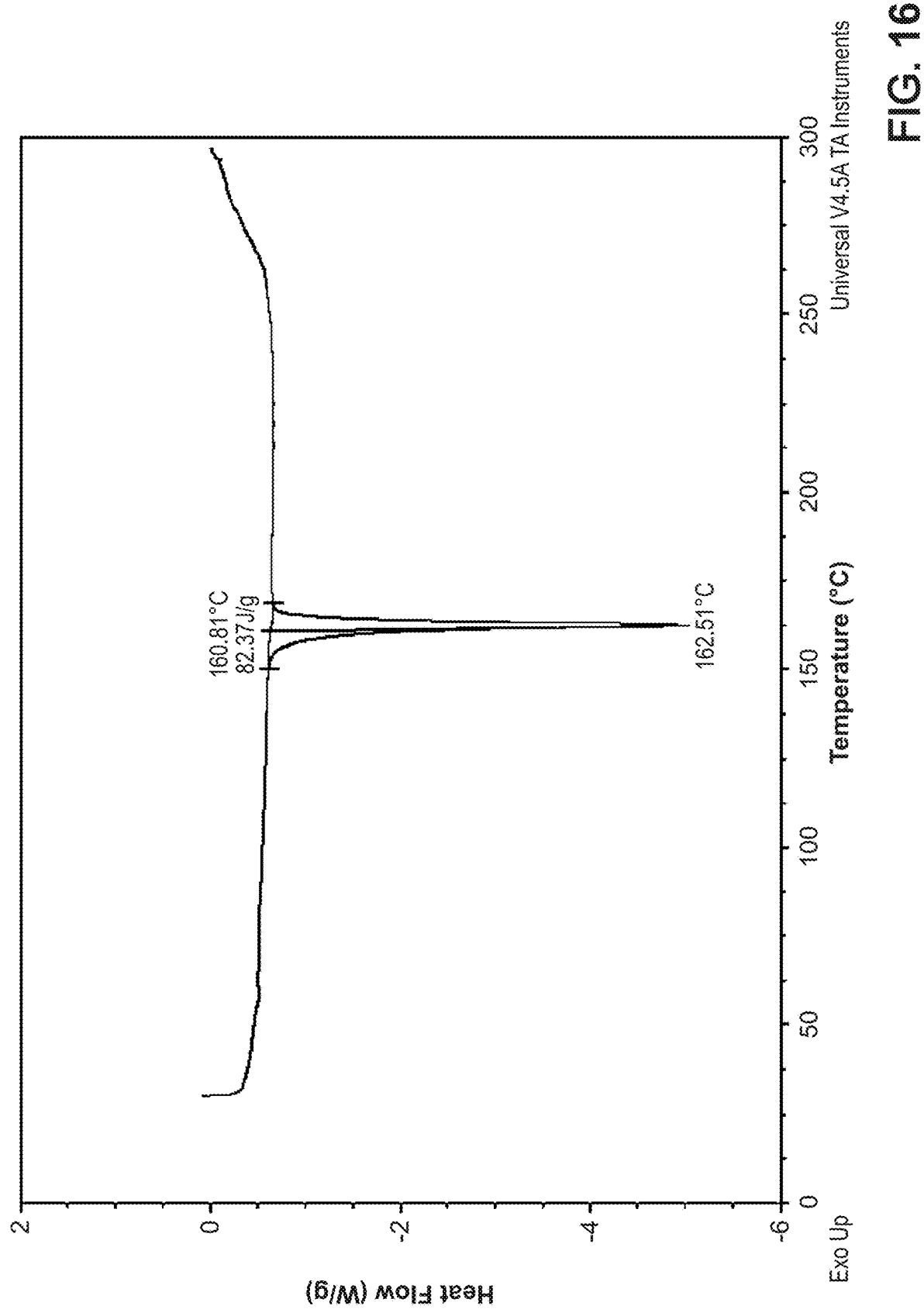
FIG. 16 depicts an exemplary DSC curve of Form 4.
Figure 18:
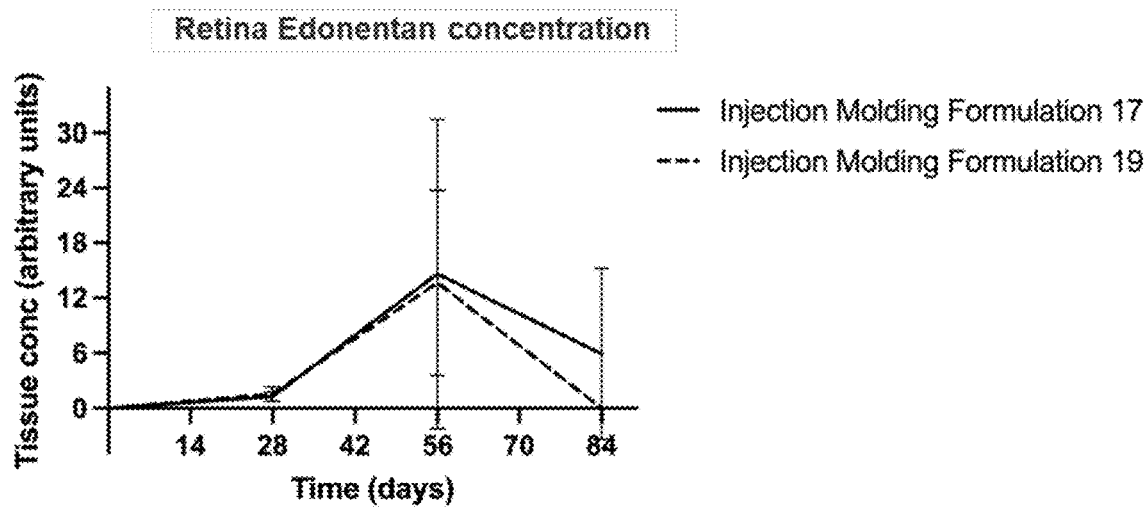
FIG. 18 depicts a time course of Edonentan retina levels during 12-week single dose intravitreal ocular pharmacokinetic study in pigmented rabbits dosed with 2 implants of injection molded product.
Figure 19:
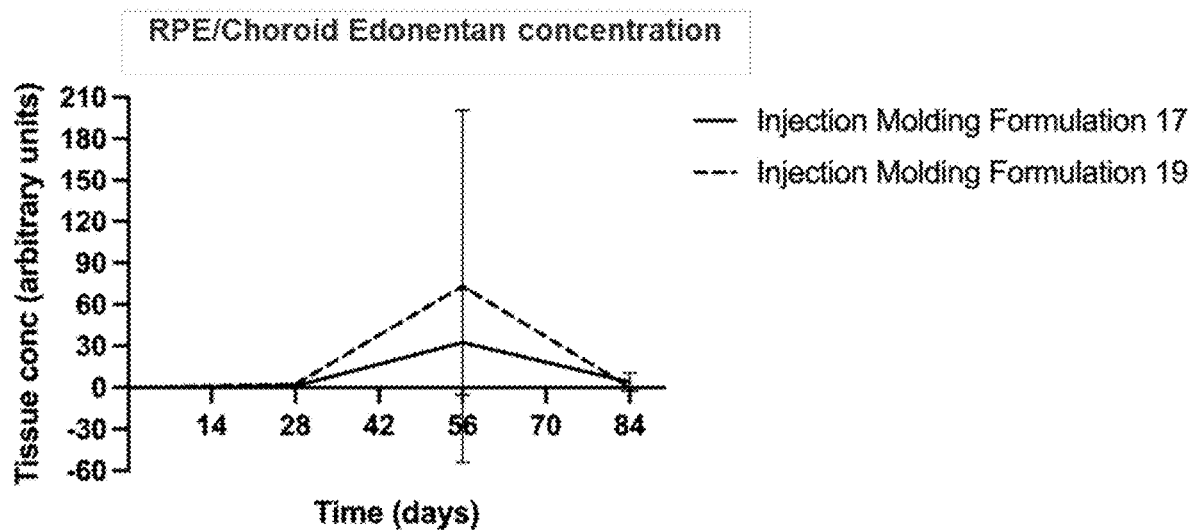
FIG. 19 depicts a time course of Edonentan RPE/choroid levels during 12-week single dose intravitreal ocular pharmacokinetic study in pigmented rabbits dosed with 2 implants of injection molded product.

Amorphous Edonentan (100 mg) was added to 2 mL of water containing 0.2 mL of tetrahydrofuran (THF). The resulting mixture was stirred at 50° C. for 24 hours, cooled and filtered to provide Form 4, which was confirmed by XRPD (FIG. 16) and DSC (FIG. 20) to be distinct from Forms 1, 2 and 3.

In an alternate method, 107 mg of amorphous Edonentan was added to 1 mL of water followed by the addition of an equivalent of KOH in 1 mL of water. The resulting solution was heated to 60° C. for 20 minutes, filtered warm and acidified with 1 mL of 0.2 N HCl. The resulting mixture was stirred for 5 hours at 60° C., cooled and filtered to give Form 4, which was confirmed by XRPD.

In an alternate method, 150 mg of Edonentan (Form 3) was added to a mixture of isopropanol and water (1 mL and 2 mL, respectively). The resulting slurry was stirred at 15° C. for 48 hours and then filtered. The sample was confirmed by an XRPD analysis to be Form 4, demonstrating that under these conditions, Form 4 is more thermodynamically stable than Form 3.

In an alternate method, 200 mg of Edonentan (Form 1) was added to a mixture of isopropanol and water (1.3 mL and 2.6 mL, respectively). The resulting solution was heated to 80° C. and stirred for 24 h, then cooled and filtered. The sample thus obtained was confirmed by an XRPD analysis to be Form 4, demonstrating that under these conditions, Form 4 is more thermodynamically stable than Form 1.

In an alternate method, 100 mg of Edonentan (amorphous) was scurried in 10 mL of water and heated to 100° C. for 40 hours. The resulting solution was cooled to ambient temperature and filtered to afford Form 4. In an alternate method, amorphous (crude) Edonentan is dissolved in 8 volumes of isopropanol at 60° C. The resulting solution is cooled to 57° C., and then a small crystal of the crystalline Form 4 is added. After 2 hours, the solution is cooled to 5° C., held for 15 hours, and filtered to afford the crystalline Form 4.

XRPD Patterns of Crystalline Forms

The XRPD patterns of crystalline Forms 1-4 are shown in FIGS. 8-12. The XRPD pattern of the crystalline form described herein was recorded using a Polycrystalline X-ray diffractometer (Bruker, D8 ADVANCE). The CuKa radiation was operating at a voltage of 40 kv and a current of 40 mA with a transmission slit of 1.0 mm and cable-stayed slit of 0.4°. A sample was placed in the center of sample holder groove and the surface of sample holder was leveled with the surface of sample holder. The data were collected over continuous scanning with a step size of 0.02° and a speed of 8°/min using the lynxeye detector.

The following Tables 13-16 list certain XRPD characteristic peaks for crystalline Forms 1-4, respectively.

TABLE 13

Exemplary XRPD patterns of crystalline Form 1

| 2θ | Intensity (counts) |
| --- | --- |
| 6.3 | 1250 |
| 7.5 | 2750 |
| 11.7 | 1400 |
| 15.1 | 2200 |
| 17.3 | 900 |

TABLE 14

Exemplary XRPD patterns of crystalline Form 2

| Angle [2θ] | Intensity (counts) |
| --- | --- |
| 9.6 | 2250 |
| 10.4 | 1500 |
| 11.1 | 600 |
| 12.3 | 750 |
| 14.6 | 1000 |
| 15.1 | 800 |
| 17.2 | 1000 |
| 19.6 | 3000 |
| 19.7 | 3000 |
| 22.0 | 1500 |
| 22.9 | 1500 |
| 23.7 | 2000 |

TABLE 15

Exemplary XRPD patterns of crystalline Form 3

| 2θ | Intensity (counts) |
| --- | --- |
| 7.8 | 2000 |
| 9.0 | 2750 |
| 11.6 | 750 |
| 15.8 | 2500 |
| 19.1 | 900 |

TABLE 16

Exemplary XRPD patterns of crystalline Form 4

| Angle [2θ] | Intensity (counts) |
| --- | --- |
| 5.6 | 1800 |
| 11.4 | 12600 |
| 14.4 | 1400 |
| 15.7 | 1200 |
| 16.8 | 1400 |
| 17.7 | 4800 |
| 19.3 | 6700 |
| 21.1 | 2900 |
| 21.9 | 2400 |
| 23.9 | 2400 |
| 24.6 | 1900 |

Physiochemical Properties of Crystalline Forms

Provided herein are exemplary physicochemical properties of crystalline forms. The melting points described herein can be measured using the following procedure:

i. Melting Point Protocol

The maximal melting point peak ($T_m$) of each crystalline form was determined using DSC. The DSC of the crystalline form described herein was measured using the TA instrument DSC Q2000. A sample (1.3010 mg) was weighed in an aluminum crucible and heated from 30° C. to 300° C. at a heating rate of 10° C./min. Temperatures at crystalline melting peak start, peak onset, peak max, and peak end were collected.

The solubility described herein can be measured using the following procedure:

ii. Solubility Analysis Protocol
1. No less than 2.0 mg samples are weighed into lower chamber of whatman miniuniprep vials (GE Healthcare). 450 µL of buffer was added into each chamber.
2. Filter pistons of miniuniprep vials are placed and compressed to the position of the liquid level to allow for contact of buffer and compound with the filter during incubation.
3. The samples are vortexed for 2 minutes followed by incubation at room temperature (about 25±2° C.) for 24 hours with shaking at 500 rpm.
4. Miniunipreps are compressed to prepare the filtrates for injection into HPLC system. All vials are inspected for visible undissolved material before filtering and for leakage after filtering.
5. Dilute supernatant with buffer by a factor of 100 folds to make diluents which are analyzed with HPLC.

Provided in Table 17 below are exemplary physicochemical properties of crystalline Forms 1-4. The physicochemical properties can be obtained using the methods described above.

TABLE 17

Exemplary physicochemical properties of crystalline Forms 1-4

| Polymorph | Solvation | $T_m$ (° C.) | Solubility pH 7.0 Phosphate Buffer (µg/mL) |
|---|---|---|---|
| Form 1 | anhydrate | 151 | 264 |
| Form 2 | monohydrate | 122 | 35 |
| Form 3 | anhydrate | 162 | 251 |
| Form 4 | anhydrate | 163 | 138 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:
1. A biodegradable ocular implant comprising:
   a biodegradable polymer containing a compound incorporated therein, wherein:
   the compound is a compound of Formula I:

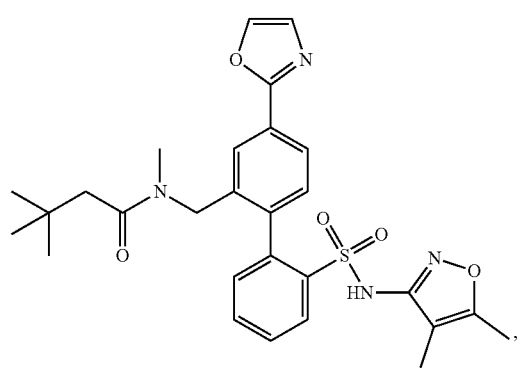

(I)

or a pharmaceutically acceptable salt thereof, wherein:
the concentration of the compound in the biodegradable polymer is about 45% w/w; and
the biodegradable polymer is [about 50% of RG503]: [about 10% of RG502]: [about 40% of RG753S], wherein said RG503 or RG502 is a poly(D,L-lactide-co-glycolide) synthesized at about 50:50 ratio of lactide to glycolide, and said RG753S is a poly(D,L-lactide-co-glycolide) synthesized at about 75:25 ratio of lactide to glycolide.

2. The biodegradable ocular implant of claim 1, wherein the implant has a diameter of about 300 μm to about 400 μm and a length of about 4 mm to about 5 mm.

3. The biodegradable ocular implant of claim 1, wherein the implant is administered as an intravitreal administration.

4. The biodegradable ocular implant of claim 1, wherein the implant is administered into the back of an eye.

* * * * *